United States Patent
Zeng et al.

(10) Patent No.: US 10,947,523 B2
(45) Date of Patent: Mar. 16, 2021

(54) BIOTECHNOLOGICAL PRODUCTION OF L-TRYPTOPHAN

(71) Applicant: Technische Universitaet Hamburg, Hamburg (DE)

(72) Inventors: An-Ping Zeng, Rosengarten (DE); Lin Chen, Hamburg (DE)

(73) Assignee: Technische Universitaet Hamburg, Hamburg (DE)

(*) Notice: Subject to any disclaimer, the term of this patent is extended or adjusted under 35 U.S.C. 154(b) by 0 days.

(21) Appl. No.: 16/763,017

(22) PCT Filed: Nov. 12, 2018

(86) PCT No.: PCT/EP2018/080908
§ 371 (c)(1),
(2) Date: May 11, 2020

(87) PCT Pub. No.: WO2019/096727
PCT Pub. Date: May 23, 2019

(65) Prior Publication Data
US 2020/0277593 A1 Sep. 3, 2020

(30) Foreign Application Priority Data
Nov. 15, 2017 (DE) .......................... 10 2017 126 895
Nov. 15, 2017 (LU) .......................................... 100521

(51) Int. Cl.
*C12N 9/88* (2006.01)
*C12P 13/22* (2006.01)
*C12N 15/00* (2006.01)

(52) U.S. Cl.
CPC .............. *C12N 9/88* (2013.01); *C12P 13/227* (2013.01); *C12Y 401/01048* (2013.01); *C12Y 401/03027* (2013.01)

(58) Field of Classification Search
CPC .......... A61L 15/24; C12N 9/0008; C12N 9/12; C12N 9/16; C12N 15/63
See application file for complete search history.

(56) References Cited

U.S. PATENT DOCUMENTS

2016/0153014 A1   6/2016   Kim et al.

FOREIGN PATENT DOCUMENTS

| CN | 106520652 A | 3/2017 |
| EP | 2803720 A | 11/2014 |

OTHER PUBLICATIONS

International Search Report dated Mar. 8, 2019, in International Application No. PCT/EP2018/080908.
Darimont, B. et al.: "Mutational Analysis of the Active Site of Indoleglycerol Phosphate Synthase From *Escherichia coli*", Protein Science, Wiley, US, vol. 7, No. 5, May 1, 1998 (May 1, 1998), pp. 1221-1232, XP000993562, ISSN: 0961-8368, Abstract, Tables 1,4.
Horng, J. S. et al.: "Cloning and characterization of the trpC gene from an aflatoxigenic strain of Aspergillus parasiticus", Applied and Environmental Microbiology, Oct. 1, 1989 (Oct. 1, 1989), pp. 2561-2568, XP055479100, United States, Retrieved from the Internet: URL: http://aem.asm.org/content/55/10/2561.full.pdf, p. 2562, Right-Hand Column, Paragraph 5; Table 1.
Yelton, Melanie M. et al.: "Developmental regulation of the Aspergillus nidulans trpC gene", Genetics, Dec. 1, 1983 (Dec. 1, 1983), pp. 7576-7580, XP055561062, Retrieved from the Internet: URL: https://europepmc.org/backend/ptpmcrender.fcgi?accid=PMC534383&blobtype=pdf, p. 7577, Right-Hand Column, Paragraph 4, Figure 1.
Chittur, S. V. et al.: "Expression and Purification of Imidazole Glycerol Phosphate Synthase from *Saccharomyces cerevisiae*", Protein Expression and Purification, Academic Press, San Diego, CA, vol. 18, No. 3, Apr. 1, 2000 (Apr. 1, 2000), pp. 366-377, XP004435552, ISSN: 1046-5928, DOI: 10.1006/PREP2000.1207, p. 371, Right-Hand Column, Paragraph 1.
Zhao, Zhi-Jun et al.: "Development of L-tryptophan production strains by defined genetic modification in *Escherichia coli*", Journal of Industrial Microbiology & Biotechnology; Official Journal of the Society for Industrial Microbiology, Springer, Berlin, DE, vol. 38, No. 12, May 4, 2011 (May 4, 2011), pp. 1921-1929, XP019982205, ISSN: 1476-5535, DOI: 10.1007/S10295-011-0978-8, p. 1925, Right-Hand column, Paragraph 3.
Chen, Lin et al.: "Discovery of feed-forward regulation in L-tryptophan biosynthesis and its use in metabolic engineering of *E. coli* for efficient tryptophan bioproduction", Metabolic Engineering, vol. 47, May 5, 2018 (May 5, 2018), pp. 434-444, XP055479146, US, ISSN: 1096-7176, DOI: 10.1016/j.ymben.2018.05.001, Figure 2, Table 2.

*Primary Examiner* — Maryam Monshipouri
(74) *Attorney, Agent, or Firm* — Patent Central LLC; Stephan A. Pendorf

(57) ABSTRACT

A biotechnological production of tryptophan and derivatives thereof, as well as a method for an enhanced microbial L-tryptophan synthesis. In one aspect the invention provides a bacterial cell being genetically modified to express anindole-3-glycerol phosphate synthase, IGPs, the IGPs being less sensitive to inhibition or even being activated by anthranilate compared to the wild type IGPs of the bacterial cell.

6 Claims, 10 Drawing Sheets
Specification includes a Sequence Listing.

SEQUENCE LISTING

```
<160> NUMBER OF SEQ ID NOS: 30

<210> SEQ ID NO 1
<211> LENGTH: 452
<212> TYPE: PRT
<213> ORGANISM: Escherichia coli

<400> SEQUENCE: 1

Met Gln Thr Val Leu Ala Lys Ile Val Ala Asp Lys Ala Ile Trp Val
1               5                   10                  15

Glu Ala Arg Lys Gln Gln Gln Pro Leu Ala Ser Phe Gln Asn Glu Val
            20                  25                  30

Gln Pro Ser Thr Arg His Phe Tyr Asp Ala Leu Gln Gly Ala Arg Thr
        35                  40                  45

Ala Phe Ile Leu Glu Cys Lys Lys Ala Ser Pro Ser Lys Gly Val Ile
    50                  55                  60

Arg Asp Asp Phe Asp Pro Ala Arg Ile Ala Ala Ile Tyr Lys His Tyr
65                  70                  75                  80

Ala Ser Ala Ile Ser Val Leu Thr Asp Glu Lys Tyr Phe Gln Gly Ser
                85                  90                  95
```

```
Phe Asn Phe Leu Pro Ile Val Ser Gln Ile Ala Pro Gln Pro Ile Leu
                100                 105                 110

Cys Lys Asp Phe Ile Ile Asp Pro Tyr Gln Ile Tyr Leu Ala Arg Tyr
            115                 120                 125

Tyr Gln Ala Asp Ala Cys Leu Leu Met Leu Ser Val Leu Asp Asp Asp
        130                 135                 140

Gln Tyr Arg Gln Leu Ala Ala Val Ala His Ser Leu Glu Met Gly Val
145                 150                 155                 160

Leu Thr Glu Val Ser Asn Glu Glu Gln Glu Arg Ala Ile Ala Leu
                165                 170                 175

Gly Ala Lys Val Val Gly Ile Asn Asn Arg Asp Leu Arg Asp Leu Ser
                180                 185                 190

Ile Asp Leu Asn Arg Thr Arg Glu Leu Ala Pro Lys Leu Gly His Asn
                195                 200                 205

Val Thr Val Ile Ser Glu Ser Gly Ile Asn Thr Tyr Ala Gln Val Arg
                210                 215                 220

Glu Leu Ser His Phe Ala Asn Gly Phe Leu Ile Gly Ser Ala Leu Met
225                 230                 235                 240

Ala His Asp Asp Leu His Ala Ala Val Arg Arg Val Leu Leu Gly Glu
                245                 250                 255

Asn Lys Val Cys Gly Leu Thr Arg Gly Gln Asp Ala Lys Ala Ala Tyr
                260                 265                 270

Asp Ala Gly Ala Ile Tyr Gly Gly Leu Ile Phe Val Ala Thr Ser Pro
                275                 280                 285

Arg Cys Val Asn Val Glu Gln Ala Gln Glu Val Met Ala Ala Ala Pro
                290                 295                 300

Leu Gln Tyr Val Gly Val Phe Arg Asn His Asp Ile Ala Asp Val Val
305                 310                 315                 320

Asp Lys Ala Lys Val Leu Ser Leu Ala Ala Val Gln Leu His Gly Asn
                325                 330                 335

Glu Glu Gln Leu Tyr Ile Asp Thr Leu Arg Glu Ala Leu Pro Ala His
                340                 345                 350

Val Ala Ile Trp Lys Ala Leu Ser Val Gly Glu Thr Leu Pro Ala Arg
                355                 360                 365

Glu Phe Gln His Val Asp Lys Tyr Val Leu Asp Asn Gly Gln Gly Gly
                370                 375                 380

Ser Gly Gln Arg Phe Asp Trp Ser Leu Leu Asn Gly Gln Ser Leu Gly
385                 390                 395                 400

Asn Val Leu Leu Ala Gly Gly Leu Gly Ala Asp Asn Cys Val Glu Ala
                405                 410                 415

Ala Gln Thr Gly Cys Ala Gly Leu Asp Phe Asn Ser Ala Val Glu Ser
                420                 425                 430

Gln Pro Gly Ile Lys Asp Ala Arg Leu Leu Ala Ser Val Phe Gln Thr
                435                 440                 445

Leu Arg Ala Tyr
            450

<210> SEQ ID NO 2
<211> LENGTH: 452
<212> TYPE: PRT
<213> ORGANISM: Artificial Sequence
<220> FEATURE:
<223> OTHER INFORMATION: EcTrpC I8V

<400> SEQUENCE: 2
```

```
Met Gln Thr Val Leu Ala Lys Val Val Ala Asp Lys Ala Ile Trp Val
1               5                   10                  15
Glu Ala Arg Lys Gln Gln Pro Leu Ala Ser Phe Gln Asn Glu Val
                20                  25                  30
Gln Pro Ser Thr Arg His Phe Tyr Asp Ala Leu Gln Gly Ala Arg Thr
            35                  40                  45
Ala Phe Ile Leu Glu Cys Lys Lys Ala Ser Pro Ser Lys Gly Val Ile
50                  55                  60
Arg Asp Asp Phe Asp Pro Ala Arg Ile Ala Ala Ile Tyr Lys His Tyr
65                  70                  75                  80
Ala Ser Ala Ile Ser Val Leu Thr Asp Glu Lys Tyr Phe Gln Gly Ser
                85                  90                  95
Phe Asn Phe Leu Pro Ile Val Ser Gln Ile Ala Pro Gln Pro Ile Leu
                100                 105                 110
Cys Lys Asp Phe Ile Ile Asp Pro Tyr Gln Ile Tyr Leu Ala Arg Tyr
            115                 120                 125
Tyr Gln Ala Asp Ala Cys Leu Leu Met Leu Ser Val Leu Asp Asp Asp
        130                 135                 140
Gln Tyr Arg Gln Leu Ala Ala Val Ala His Ser Leu Glu Met Gly Val
145                 150                 155                 160
Leu Thr Glu Val Ser Asn Glu Glu Gln Glu Arg Ala Ile Ala Leu
                165                 170                 175
Gly Ala Lys Val Val Gly Ile Asn Asn Arg Asp Leu Arg Asp Leu Ser
            180                 185                 190
Ile Asp Leu Asn Arg Thr Arg Glu Leu Ala Pro Lys Leu Gly His Asn
        195                 200                 205
Val Thr Val Ile Ser Glu Ser Gly Ile Asn Thr Tyr Ala Gln Val Arg
210                 215                 220
Glu Leu Ser His Phe Ala Asn Gly Phe Leu Ile Gly Ser Ala Leu Met
225                 230                 235                 240
Ala His Asp Asp Leu His Ala Ala Val Arg Arg Val Leu Leu Gly Glu
            245                 250                 255
Asn Lys Val Cys Gly Leu Thr Arg Gly Gln Asp Ala Lys Ala Ala Tyr
        260                 265                 270
Asp Ala Gly Ala Ile Tyr Gly Gly Leu Ile Phe Val Ala Thr Ser Pro
    275                 280                 285
Arg Cys Val Asn Val Glu Gln Ala Gln Glu Val Met Ala Ala Ala Pro
290                 295                 300
Leu Gln Tyr Val Gly Val Phe Arg Asn His Asp Ile Ala Asp Val Val
305                 310                 315                 320
Asp Lys Ala Lys Val Leu Ser Leu Ala Ala Val Gln Leu His Gly Asn
            325                 330                 335
Glu Glu Gln Leu Tyr Ile Asp Thr Leu Arg Glu Ala Leu Pro Ala His
        340                 345                 350
Val Ala Ile Trp Lys Ala Leu Ser Val Gly Glu Thr Leu Pro Ala Arg
    355                 360                 365
Glu Phe Gln His Val Asp Lys Tyr Val Leu Asp Asn Gly Gln Gly Gly
370                 375                 380
Ser Gly Gln Arg Phe Asp Trp Ser Leu Leu Asn Gly Gln Ser Leu Gly
385                 390                 395                 400
Asn Val Leu Leu Ala Gly Gly Leu Gly Ala Asp Asn Cys Val Glu Ala
            405                 410                 415
```

```
Ala Gln Thr Gly Cys Ala Gly Leu Asp Phe Asn Ser Ala Val Glu Ser
                420                 425                 430

Gln Pro Gly Ile Lys Asp Ala Arg Leu Leu Ala Ser Val Phe Gln Thr
                435                 440                 445

Leu Arg Ala Tyr
    450

<210> SEQ ID NO 3
<211> LENGTH: 452
<212> TYPE: PRT
<213> ORGANISM: Artificial Sequence
<220> FEATURE:
<223> OTHER INFORMATION: EcTrpC S60A

<400> SEQUENCE: 3

Met Gln Thr Val Leu Ala Lys Ile Val Ala Asp Lys Ala Ile Trp Val
1               5                   10                  15

Glu Ala Arg Lys Gln Gln Pro Leu Ala Ser Phe Gln Asn Glu Val
                20                  25                  30

Gln Pro Ser Thr Arg His Phe Tyr Asp Ala Leu Gln Gly Ala Arg Thr
                35                  40                  45

Ala Phe Ile Leu Glu Cys Lys Lys Ala Ser Pro Ala Lys Gly Val Ile
            50                  55                  60

Arg Asp Asp Phe Asp Pro Ala Arg Ile Ala Ala Ile Tyr Lys His Tyr
65                  70                  75                  80

Ala Ser Ala Ile Ser Val Leu Thr Asp Glu Lys Tyr Phe Gln Gly Ser
                85                  90                  95

Phe Asn Phe Leu Pro Ile Val Ser Gln Ile Ala Pro Gln Pro Ile Leu
                100                 105                 110

Cys Lys Asp Phe Ile Ile Asp Pro Tyr Gln Ile Tyr Leu Ala Arg Tyr
                115                 120                 125

Tyr Gln Ala Asp Ala Cys Leu Leu Met Leu Ser Val Leu Asp Asp Asp
    130                 135                 140

Gln Tyr Arg Gln Leu Ala Ala Val Ala His Ser Leu Glu Met Gly Val
145                 150                 155                 160

Leu Thr Glu Val Ser Asn Glu Glu Glu Gln Glu Arg Ala Ile Ala Leu
                165                 170                 175

Gly Ala Lys Val Val Gly Ile Asn Asn Arg Asp Leu Arg Asp Leu Ser
                180                 185                 190

Ile Asp Leu Asn Arg Thr Arg Glu Leu Ala Pro Lys Leu Gly His Asn
                195                 200                 205

Val Thr Val Ile Ser Glu Ser Gly Ile Asn Thr Tyr Ala Gln Val Arg
    210                 215                 220

Glu Leu Ser His Phe Ala Asn Gly Phe Leu Ile Gly Ser Ala Leu Met
225                 230                 235                 240

Ala His Asp Asp Leu His Ala Ala Val Arg Arg Val Leu Leu Gly Glu
                245                 250                 255

Asn Lys Val Cys Gly Leu Thr Arg Gly Gln Asp Ala Lys Ala Ala Tyr
                260                 265                 270

Asp Ala Gly Ala Ile Tyr Gly Gly Leu Ile Phe Val Ala Thr Ser Pro
                275                 280                 285

Arg Cys Val Asn Val Glu Gln Ala Gln Glu Val Met Ala Ala Ala Pro
    290                 295                 300

Leu Gln Tyr Val Gly Val Phe Arg Asn His Asp Ile Ala Asp Val Val
305                 310                 315                 320
```

```
Asp Lys Ala Lys Val Leu Ser Leu Ala Ala Val Gln Leu His Gly Asn
            325                 330                 335

Glu Glu Gln Leu Tyr Ile Asp Thr Leu Arg Glu Ala Leu Pro Ala His
        340                 345                 350

Val Ala Ile Trp Lys Ala Leu Ser Val Gly Glu Thr Leu Pro Ala Arg
            355                 360                 365

Glu Phe Gln His Val Asp Lys Tyr Val Leu Asp Asn Gly Gln Gly Gly
    370                 375                 380

Ser Gly Gln Arg Phe Asp Trp Ser Leu Leu Asn Gly Gln Ser Leu Gly
385                 390                 395                 400

Asn Val Leu Leu Ala Gly Gly Leu Gly Ala Asp Asn Cys Val Glu Ala
                405                 410                 415

Ala Gln Thr Gly Cys Ala Gly Leu Asp Phe Asn Ser Ala Val Glu Ser
            420                 425                 430

Gln Pro Gly Ile Lys Asp Ala Arg Leu Leu Ala Ser Val Phe Gln Thr
        435                 440                 445

Leu Arg Ala Tyr
    450

<210> SEQ ID NO 4
<211> LENGTH: 452
<212> TYPE: PRT
<213> ORGANISM: Artificial Sequence
<220> FEATURE:
<223> OTHER INFORMATION: EcTrpC S60G

<400> SEQUENCE: 4

Met Gln Thr Val Leu Ala Lys Ile Val Ala Asp Lys Ala Ile Trp Val
1               5                   10                  15

Glu Ala Arg Lys Gln Gln Gln Pro Leu Ala Ser Phe Gln Asn Glu Val
            20                  25                  30

Gln Pro Ser Thr Arg His Phe Tyr Asp Ala Leu Gln Gly Ala Arg Thr
        35                  40                  45

Ala Phe Ile Leu Glu Cys Lys Lys Ala Ser Pro Gly Lys Gly Val Ile
    50                  55                  60

Arg Asp Asp Phe Asp Pro Ala Arg Ile Ala Ala Ile Tyr Lys His Tyr
65                  70                  75                  80

Ala Ser Ala Ile Ser Val Leu Thr Asp Glu Lys Tyr Phe Gln Gly Ser
                85                  90                  95

Phe Asn Phe Leu Pro Ile Val Ser Gln Ile Ala Pro Gln Pro Ile Leu
            100                 105                 110

Cys Lys Asp Phe Ile Ile Asp Pro Tyr Gln Ile Tyr Leu Ala Arg Tyr
        115                 120                 125

Tyr Gln Ala Asp Ala Cys Leu Leu Met Leu Ser Val Leu Asp Asp Asp
    130                 135                 140

Gln Tyr Arg Gln Leu Ala Ala Val Ala His Ser Leu Glu Met Gly Val
145                 150                 155                 160

Leu Thr Glu Val Ser Asn Glu Glu Glu Gln Glu Arg Ala Ile Ala Leu
                165                 170                 175

Gly Ala Lys Val Val Gly Ile Asn Asn Arg Asp Leu Arg Asp Leu Ser
            180                 185                 190

Ile Asp Leu Asn Arg Thr Arg Glu Leu Ala Pro Lys Leu Gly His Asn
        195                 200                 205

Val Thr Val Ile Ser Glu Ser Gly Ile Asn Thr Tyr Ala Gln Val Arg
    210                 215                 220
```

```
Glu Leu Ser His Phe Ala Asn Gly Phe Leu Ile Gly Ser Ala Leu Met
225                 230                 235                 240

Ala His Asp Asp Leu His Ala Ala Val Arg Arg Val Leu Leu Gly Glu
            245                 250                 255

Asn Lys Val Cys Gly Leu Thr Arg Gly Gln Asp Ala Lys Ala Ala Tyr
            260                 265                 270

Asp Ala Gly Ala Ile Tyr Gly Gly Leu Ile Phe Val Ala Thr Ser Pro
            275                 280                 285

Arg Cys Val Asn Val Glu Gln Ala Gln Glu Val Met Ala Ala Ala Pro
            290                 295                 300

Leu Gln Tyr Val Gly Val Phe Arg Asn His Asp Ile Ala Asp Val Val
305                 310                 315                 320

Asp Lys Ala Lys Val Leu Ser Leu Ala Ala Val Gln Leu His Gly Asn
            325                 330                 335

Glu Glu Gln Leu Tyr Ile Asp Thr Leu Arg Glu Ala Leu Pro Ala His
            340                 345                 350

Val Ala Ile Trp Lys Ala Leu Ser Val Gly Glu Thr Leu Pro Ala Arg
            355                 360                 365

Glu Phe Gln His Val Asp Lys Tyr Val Leu Asp Asn Gly Gln Gly Gly
            370                 375                 380

Ser Gly Gln Arg Phe Asp Trp Ser Leu Leu Asn Gly Gln Ser Leu Gly
385                 390                 395                 400

Asn Val Leu Leu Ala Gly Gly Leu Gly Ala Asp Asn Cys Val Glu Ala
            405                 410                 415

Ala Gln Thr Gly Cys Ala Gly Leu Asp Phe Asn Ser Ala Val Glu Ser
            420                 425                 430

Gln Pro Gly Ile Lys Asp Ala Arg Leu Leu Ala Ser Val Phe Gln Thr
            435                 440                 445

Leu Arg Ala Tyr
            450

<210> SEQ ID NO 5
<211> LENGTH: 452
<212> TYPE: PRT
<213> ORGANISM: Artificial Sequence
<220> FEATURE:
<223> OTHER INFORMATION: EcTrpC L188F

<400> SEQUENCE: 5

Met Gln Thr Val Leu Ala Lys Ile Val Ala Asp Lys Ala Ile Trp Val
1               5                   10                  15

Glu Ala Arg Lys Gln Gln Gln Pro Leu Ala Ser Phe Gln Asn Glu Val
            20                  25                  30

Gln Pro Ser Thr Arg His Phe Tyr Asp Ala Leu Gln Gly Ala Arg Thr
        35                  40                  45

Ala Phe Ile Leu Glu Cys Lys Lys Ala Ser Pro Ser Lys Gly Val Ile
    50                  55                  60

Arg Asp Asp Phe Asp Pro Ala Arg Ile Ala Ala Ile Tyr Lys His Tyr
65                  70                  75                  80

Ala Ser Ala Ile Ser Val Leu Thr Asp Glu Lys Tyr Phe Gln Gly Ser
            85                  90                  95

Phe Asn Phe Leu Pro Ile Val Ser Gln Ile Ala Pro Gln Pro Ile Leu
            100                 105                 110

Cys Lys Asp Phe Ile Ile Asp Pro Tyr Gln Ile Tyr Leu Ala Arg Tyr
            115                 120                 125
```

```
Tyr Gln Ala Asp Ala Cys Leu Leu Met Leu Ser Val Leu Asp Asp
    130                 135                 140

Gln Tyr Arg Gln Leu Ala Ala Val Ala His Ser Leu Glu Met Gly Val
145                 150                 155                 160

Leu Thr Glu Val Ser Asn Glu Glu Gln Glu Arg Ala Ile Ala Leu
                165                 170                 175

Gly Ala Lys Val Val Gly Ile Asn Asn Arg Asp Phe Arg Asp Leu Ser
                180                 185                 190

Ile Asp Leu Asn Arg Thr Arg Glu Leu Ala Pro Lys Leu Gly His Asn
                195                 200                 205

Val Thr Val Ile Ser Glu Ser Gly Ile Asn Thr Tyr Ala Gln Val Arg
    210                 215                 220

Glu Leu Ser His Phe Ala Asn Gly Phe Leu Ile Gly Ser Ala Leu Met
225                 230                 235                 240

Ala His Asp Asp Leu His Ala Ala Val Arg Arg Val Leu Leu Gly Glu
                245                 250                 255

Asn Lys Val Cys Gly Leu Thr Arg Gly Gln Asp Ala Lys Ala Ala Tyr
                260                 265                 270

Asp Ala Gly Ala Ile Tyr Gly Gly Leu Ile Phe Val Ala Thr Ser Pro
                275                 280                 285

Arg Cys Val Asn Val Glu Gln Ala Gln Glu Val Met Ala Ala Ala Pro
    290                 295                 300

Leu Gln Tyr Val Gly Val Phe Arg Asn His Asp Ile Ala Asp Val Val
305                 310                 315                 320

Asp Lys Ala Lys Val Leu Ser Leu Ala Ala Val Gln Leu His Gly Asn
                325                 330                 335

Glu Glu Gln Leu Tyr Ile Asp Thr Leu Arg Glu Ala Leu Pro Ala His
                340                 345                 350

Val Ala Ile Trp Lys Ala Leu Ser Val Gly Glu Thr Leu Pro Ala Arg
    355                 360                 365

Glu Phe Gln His Val Asp Lys Tyr Val Leu Asp Asn Gly Gln Gly Gly
370                 375                 380

Ser Gly Gln Arg Phe Asp Trp Ser Leu Leu Asn Gly Gln Ser Leu Gly
385                 390                 395                 400

Asn Val Leu Leu Ala Gly Gly Leu Gly Ala Asp Asn Cys Val Glu Ala
                405                 410                 415

Ala Gln Thr Gly Cys Ala Gly Leu Asp Phe Asn Ser Ala Val Glu Ser
                420                 425                 430

Gln Pro Gly Ile Lys Asp Ala Arg Leu Leu Ala Ser Val Phe Gln Thr
                435                 440                 445

Leu Arg Ala Tyr
    450

<210> SEQ ID NO 6
<211> LENGTH: 484
<212> TYPE: PRT
<213> ORGANISM: Saccharomyces cerevisiae

<400> SEQUENCE: 6

Met Ser Val His Ala Ala Thr Asn Pro Ile Asn Lys His Val Val Leu
1               5                   10                  15

Ile Asp Asn Tyr Asp Ser Phe Thr Trp Asn Val Tyr Glu Tyr Leu Cys
                20                  25                  30

Gln Glu Gly Ala Lys Val Ser Val Tyr Arg Asn Asp Ala Ile Thr Val
                35                  40                  45
```

-continued

```
Pro Glu Ile Ala Ala Leu Asn Pro Asp Thr Leu Leu Ile Ser Pro Gly
    50                  55                  60

Pro Gly His Pro Lys Thr Asp Ser Gly Ile Ser Arg Asp Cys Ile Arg
65                  70                  75                  80

Tyr Phe Thr Gly Lys Ile Pro Val Phe Gly Ile Cys Met Gly Gln Gln
                85                  90                  95

Cys Met Phe Asp Val Phe Gly Gly Glu Val Ala Tyr Ala Gly Glu Ile
                100                 105                 110

Val His Gly Lys Thr Ser Pro Ile Ser His Asp Asn Cys Gly Ile Phe
            115                 120                 125

Lys Asn Val Pro Gln Gly Ile Ala Val Thr Arg Tyr His Ser Leu Ala
130                 135                 140

Gly Thr Glu Ser Ser Leu Pro Ser Cys Leu Lys Val Thr Ala Ser Thr
145                 150                 155                 160

Glu Asn Gly Ile Ile Met Gly Val Arg His Lys Lys Tyr Thr Val Glu
                165                 170                 175

Gly Val Gln Phe His Pro Glu Ser Ile Leu Thr Glu Gly His Leu
                180                 185                 190

Met Ile Arg Asn Ile Leu Asn Val Ser Gly Gly Thr Trp Glu Glu Asn
    195                 200                 205

Lys Ser Ser Pro Ser Asn Ser Ile Leu Asp Arg Ile Tyr Ala Arg Arg
    210                 215                 220

Lys Ile Asp Val Asn Glu Gln Ser Lys Ile Pro Gly Phe Thr Phe Gln
225                 230                 235                 240

Asp Leu Gln Ser Asn Tyr Asp Leu Gly Leu Ala Pro Pro Leu Gln Asp
                245                 250                 255

Phe Tyr Thr Val Leu Ser Ser His Lys Arg Ala Val Val Leu Ala
                260                 265                 270

Glu Val Lys Arg Ala Ser Pro Ser Lys Gly Pro Ile Cys Leu Lys Ala
            275                 280                 285

Val Ala Ala Glu Gln Ala Leu Lys Tyr Ala Glu Ala Gly Ala Ser Ala
290                 295                 300

Ile Ser Val Leu Thr Glu Pro His Trp Phe His Gly Ser Leu Gln Asp
305                 310                 315                 320

Leu Val Asn Val Arg Lys Ile Leu Asp Leu Lys Phe Pro Pro Lys Glu
                325                 330                 335

Arg Pro Cys Val Leu Arg Lys Glu Phe Ile Phe Ser Lys Tyr Gln Ile
                340                 345                 350

Leu Glu Ala Arg Leu Ala Gly Ala Asp Thr Val Leu Leu Ile Val Lys
            355                 360                 365

Met Leu Ser Gln Pro Leu Leu Lys Glu Leu Tyr Ser Tyr Ser Lys Asp
    370                 375                 380

Leu Asn Met Glu Pro Leu Val Glu Val Asn Ser Lys Glu Glu Leu Gln
385                 390                 395                 400

Arg Ala Leu Glu Ile Gly Ala Lys Val Val Gly Val Asn Asn Arg Asp
                405                 410                 415

Leu His Ser Phe Asn Val Asp Leu Asn Thr Thr Ser Asn Leu Val Glu
                420                 425                 430

Ser Ile Pro Lys Asp Val Leu Leu Ile Ala Leu Ser Gly Ile Thr Thr
            435                 440                 445

Arg Asp Asp Ala Glu Lys Tyr Lys Lys Glu Gly Val His Gly Phe Leu
    450                 455                 460
```

Val Gly Glu Ala Leu Met Lys Ser Thr Asp Val Lys Lys Phe Ile His
465                 470                 475                 480

Glu Leu Cys Glu

<210> SEQ ID NO 7
<211> LENGTH: 770
<212> TYPE: PRT
<213> ORGANISM: Aspergillus niger

<400> SEQUENCE: 7

Met Ala Asp Ser Gly Leu Val Asp His Ser Pro His Pro Thr Lys
1               5                   10                  15

Ala Ala Gln Leu Asn Thr Ala Ser Asn Val Ile Leu Ile Asp Asn Tyr
            20                  25                  30

Asp Ser Phe Thr Trp Asn Val Tyr Gln Tyr Leu Val Leu Glu Gly Ala
        35                  40                  45

Thr Val Asn Val Phe Arg Asn Asp Gln Ile Thr Leu Glu Glu Leu Ile
    50                  55                  60

Ala Lys Lys Pro Thr Gln Leu Val Ile Ser Pro Gly Pro Gly His Pro
65                  70                  75                  80

Glu Thr Asp Ala Gly Ile Ser Ser Ala Ala Ile Gln Tyr Phe Ser Gly
                85                  90                  95

Lys Ile Pro Ile Phe Gly Val Cys Met Gly Gln Gln Cys Ile Ile Thr
            100                 105                 110

Cys Phe Gly Gly Lys Val Asp Val Thr Gly Glu Ile Leu His Gly Lys
        115                 120                 125

Thr Ser Ala Leu Lys His Asp Gly Lys Gly Ala Tyr Glu Gly Leu Pro
    130                 135                 140

Asp Ser Leu Ala Val Thr Arg Tyr His Ser Leu Ala Gly Thr His Ala
145                 150                 155                 160

Thr Ile Pro Asp Cys Leu Glu Val Ser Ser Val Gln Leu Thr Asp
                165                 170                 175

Asp Ser Asn Lys Asp Val Ile Met Gly Val Arg His Lys Lys Leu Ala
            180                 185                 190

Val Glu Gly Val Gln Phe His Pro Glu Ser Ile Leu Thr Glu Tyr Gly
        195                 200                 205

Arg Thr Met Phe Arg Asn Phe Leu Lys Leu Thr Ala Gly Thr Trp Glu
    210                 215                 220

Gly Asn Gly Lys His Phe Asp Glu Gln Ser Asn Thr Thr Lys Ala Thr
225                 230                 235                 240

Val Ser Ser Asn Thr Ala Pro Lys Thr Asp Lys Lys Leu Ser Ile Leu
                245                 250                 255

Glu Arg Ile Tyr Asp His Arg Arg Ala Ala Val Ala Val Gln Lys Thr
            260                 265                 270

Ile Pro Ser Gln Arg Pro Ala Asp Leu Gln Ala Ala Tyr Asp Leu Asn
        275                 280                 285

Leu Ala Pro Pro Gln Val Pro Phe Pro Ala Arg Leu Arg Gln Ser Pro
    290                 295                 300

Tyr Pro Leu Ser Leu Met Ala Glu Ile Lys Arg Ala Ser Pro Ser Lys
305                 310                 315                 320

Gly Met Ile Ala Glu Asn Ala Cys Ala Pro Ala Gln Ala Arg Gln Tyr
                325                 330                 335

Ala Lys Ala Gly Ala Ser Val Ile Ser Val Leu Thr Glu Pro Glu Trp
            340                 345                 350

```
Phe Lys Gly Ser Ile Asp Asp Leu Arg Ala Val Arg Gln Ser Leu Glu
            355                 360                 365
Gly Leu Thr Asn Arg Pro Ala Ile Leu Arg Lys Glu Phe Val Phe Asp
        370                 375                 380
Glu Tyr Gln Ile Leu Glu Ala Arg Leu Ala Gly Ala Asp Thr Val Leu
385                 390                 395                 400
Leu Ile Val Lys Met Leu Ser Val Glu Leu Leu Thr Arg Leu Tyr His
                405                 410                 415
Tyr Ser Arg Ser Leu Gly Met Glu Pro Leu Val Glu Val Asn Thr Pro
            420                 425                 430
Glu Glu Met Lys Ile Ala Val Asp Leu Gly Ala Glu Val Ile Gly Val
        435                 440                 445
Asn Asn Arg Asp Leu Thr Ser Phe Glu Val Asp Leu Gly Thr Thr Ser
450                 455                 460
Arg Leu Met Asp Gln Val Pro Ser Ser Thr Ile Val Cys Ala Leu Ser
465                 470                 475                 480
Gly Ile Ser Gly Pro Lys Asp Val Glu Ala Tyr Lys Lys Glu Gly Val
            485                 490                 495
Lys Ala Ile Leu Val Gly Glu Ala Leu Met Arg Ala Ala Asp Thr Ala
                500                 505                 510
Ala Phe Ile Ala Glu Leu Leu Gly Gly Ser Ser Gln Asn Val Ser Lys
            515                 520                 525
Glu Ser Arg Ser Ser Pro Leu Val Lys Ile Cys Gly Thr Arg Ser Glu
        530                 535                 540
Glu Ala Ala Arg Ala Ala Ile Glu Ala Gly Ala Asp Leu Ile Gly Ile
545                 550                 555                 560
Ile Met Val Gln Gly Arg Thr Arg Cys Val Pro Asp Asp Val Ala Leu
                565                 570                 575
Arg Ile Ser Gln Val Val Lys Ser Thr Pro Lys Pro Ala Gly Gln Thr
            580                 585                 590
Pro Pro Thr Ser Gln Gly Thr Pro Ala Ala Ala Ser Val Glu Tyr Phe
        595                 600                 605
Asp His Ser Ala Arg Ile Leu Arg His Pro Ser Arg Ala Leu Leu Val
610                 615                 620
Gly Val Phe Gln Asn Gln Pro Leu Asp Tyr Ile Leu Ser Gln Gln Gln
625                 630                 635                 640
Lys Leu Gly Leu Asp Val Val Gln Leu His Gly Ser Glu Pro Leu Glu
                645                 650                 655
Trp Ala Lys Leu Ile Pro Val Pro Val Ile Arg Lys Phe Gly Leu Asp
            660                 665                 670
Glu Pro Ala Ile Ala Arg Arg Ala Tyr His Ser Leu Pro Leu Leu Asp
        675                 680                 685
Ser Gly Val Gly Gly Thr Gly Glu Leu Leu Asp Gln Ser Arg Val Gln
690                 695                 700
Asn Val Leu Asp Lys Asp Ser Gly Leu Arg Val Ile Leu Ala Gly Gly
705                 710                 715                 720
Leu Asp Pro Thr Asn Val Ala Gly Ile Val Gln Lys Leu Gly Glu Ser
                725                 730                 735
Gly Arg Lys Val Val Gly Val Asp Val Ser Ser Gly Val Glu Ser Asp
            740                 745                 750
Gly Ala Gln Asp Val Gly Lys Ile Arg Ala Phe Val Gln Ala Val Arg
        755                 760                 765

Gly Leu
```

```
<210> SEQ ID NO 8
<211> LENGTH: 50
<212> TYPE: DNA
<213> ORGANISM: Artificial Sequence
<220> FEATURE:
<223> OTHER INFORMATION: Primer SmaI-trpE

<400> SEQUENCE: 8
ttgttcccgg gtataaagga ggccatccat gcaaacacaa aaaccgactc         50

<210> SEQ ID NO 9
<211> LENGTH: 36
<212> TYPE: DNA
<213> ORGANISM: Artificial Sequence
<220> FEATURE:
<223> OTHER INFORMATION: Primer trpE-XbaI

<400> SEQUENCE: 9
gcagaatcta gatcatcaga aagtctcctg tgcatg                       36

<210> SEQ ID NO 10
<211> LENGTH: 70
<212> TYPE: DNA
<213> ORGANISM: Artificial Sequence
<220> FEATURE:
<223> OTHER INFORMATION: Primer trpC-O1

<400> SEQUENCE: 10
gcgctacagg gtgcgcgcac ggcgtttatt ctggagtgca agaaagcgtc gttgacagct     60
agctcagtcc                                                            70

<210> SEQ ID NO 11
<211> LENGTH: 70
<212> TYPE: DNA
<213> ORGANISM: Artificial Sequence
<220> FEATURE:
<223> OTHER INFORMATION: Primer trpC-O2

<400> SEQUENCE: 11
gatgccggat tcgctgatta ccgtcacgtt gtgccccagt ttcggcgcaa atttgatgcc     60
tgggcatgcg                                                            70

<210> SEQ ID NO 12
<211> LENGTH: 20
<212> TYPE: DNA
<213> ORGANISM: Artificial Sequence
<220> FEATURE:
<223> OTHER INFORMATION: Primer trpC-INF

<400> SEQUENCE: 12
atgcaaaccg ttttagcgaa                                         20

<210> SEQ ID NO 13
<211> LENGTH: 20
<212> TYPE: DNA
<213> ORGANISM: Artificial Sequence
<220> FEATURE:
<223> OTHER INFORMATION: Primer trpC-INR

<400> SEQUENCE: 13
caaatcgtca tgggccatca                                         20
```

```
<210> SEQ ID NO 14
<211> LENGTH: 37
<212> TYPE: DNA
<213> ORGANISM: Artificial Sequence
<220> FEATURE:
<223> OTHER INFORMATION: Primer NdeI-eIGPs

<400> SEQUENCE: 14
gcaacgcata tgcaaaccgt tttagcgaaa atcgtcg                               37

<210> SEQ ID NO 15
<211> LENGTH: 37
<212> TYPE: DNA
<213> ORGANISM: Artificial Sequence
<220> FEATURE:
<223> OTHER INFORMATION: Primer eIGPs-XhoI

<400> SEQUENCE: 15
agtcgcctcg agtactttat tctcacccag caacacc                               37

<210> SEQ ID NO 16
<211> LENGTH: 74
<212> TYPE: DNA
<213> ORGANISM: Artificial Sequence
<220> FEATURE:
<223> OTHER INFORMATION: Primer EcoRI-6H-trpC

<400> SEQUENCE: 16
cggcgcgaat tcagaaggag atatacatat gcaccaccac caccaccacc aaaccgtttt      60
agcgaaaatc gtcg                                                        74

<210> SEQ ID NO 17
<211> LENGTH: 31
<212> TYPE: DNA
<213> ORGANISM: Artificial Sequence
<220> FEATURE:
<223> OTHER INFORMATION: Primer trpC-XbaI

<400> SEQUENCE: 17
agcgtctcta gacttaatat gcgcgcagcg t                                     31

<210> SEQ ID NO 18
<211> LENGTH: 41
<212> TYPE: DNA
<213> ORGANISM: Artificial Sequence
<220> FEATURE:
<223> OTHER INFORMATION: Primer eIGPs-XbaI

<400> SEQUENCE: 18
agcgtctcta gacttatact ttattctcac ccagcaacac c                          41

<210> SEQ ID NO 19
<211> LENGTH: 22
<212> TYPE: DNA
<213> ORGANISM: Artificial Sequence
<220> FEATURE:
<223> OTHER INFORMATION: Primer eIGPs-I8X-F

<400> SEQUENCE: 19
gcagacaagg cgatttgggt ag                                               22

<210> SEQ ID NO 20
<211> LENGTH: 27
<212> TYPE: DNA
<213> ORGANISM: Artificial Sequence
<220> FEATURE:
```

```
<223> OTHER INFORMATION: Primer eIGPs-I8A-R

<400> SEQUENCE: 20
gacggctttc gctaaaacgg tttgcat                                              27

<210> SEQ ID NO 21
<211> LENGTH: 27
<212> TYPE: DNA
<213> ORGANISM: Artificial Sequence
<220> FEATURE:
<223> OTHER INFORMATION: Primer eIGPs-I8V-R

<400> SEQUENCE: 21
gacgactttc gctaaaacgg tttgcat                                              27

<210> SEQ ID NO 22
<211> LENGTH: 21
<212> TYPE: DNA
<213> ORGANISM: Artificial Sequence
<220> FEATURE:
<223> OTHER INFORMATION: Primer eIGPs-S60A_F

<400> SEQUENCE: 22
gcaaaaggcg tgatccgtga t                                                    21

<210> SEQ ID NO 23
<211> LENGTH: 20
<212> TYPE: DNA
<213> ORGANISM: Artificial Sequence
<220> FEATURE:
<223> OTHER INFORMATION: Primer eIGPs-S60A_R

<400> SEQUENCE: 23
cggcgacgct tccttgcact                                                      20

<210> SEQ ID NO 24
<211> LENGTH: 28
<212> TYPE: DNA
<213> ORGANISM: Artificial Sequence
<220> FEATURE:
<223> OTHER INFORMATION: Primer eIGPs-S60G_F

<400> SEQUENCE: 24
tcgccgggaa aaggcgtgat ccgtgatg                                             28

<210> SEQ ID NO 25
<211> LENGTH: 19
<212> TYPE: DNA
<213> ORGANISM: Artificial Sequence
<220> FEATURE:
<223> OTHER INFORMATION: Primer eIGPs-S60G_R

<400> SEQUENCE: 25
cgctttcttg cactccaga                                                       19

<210> SEQ ID NO 26
<211> LENGTH: 21
<212> TYPE: DNA
<213> ORGANISM: Artificial Sequence
<220> FEATURE:
<223> OTHER INFORMATION: Primer eIGPs-L188A_R

<400> SEQUENCE: 26
atcgcggttg ttgatgccaa c                                                    21
```

-continued

```
<210> SEQ ID NO 27
<211> LENGTH: 20
<212> TYPE: DNA
<213> ORGANISM: Artificial Sequence
<220> FEATURE:
<223> OTHER INFORMATION: Primer eIGPs-L188A_F

<400> SEQUENCE: 27
gcgcgtgatt tgtcgattga                                              20

<210> SEQ ID NO 28
<211> LENGTH: 19
<212> TYPE: DNA
<213> ORGANISM: Artificial Sequence
<220> FEATURE:
<223> OTHER INFORMATION: Primer eIGPs-L188F_R

<400> SEQUENCE: 28
gttgttgatg ccaacgacc                                               19

<210> SEQ ID NO 29
<211> LENGTH: 34
<212> TYPE: DNA
<213> ORGANISM: Artificial Sequence
<220> FEATURE:
<223> OTHER INFORMATION: Primer eIGPs-L188F_F

<400> SEQUENCE: 29
cgcgattttc gtgatttgtc gattgatctc aacc                              34

<210> SEQ ID NO 30
<211> LENGTH: 452
<212> TYPE: PRT
<213> ORGANISM: Artificial Sequence
<220> FEATURE:
<223> OTHER INFORMATION: EcTrpC S58Q P59V S60F K61Q

<400> SEQUENCE: 30
```

Met Gln Thr Val Leu Ala Lys Ile Val Ala Asp Lys Ala Ile Trp Val
1               5                   10                  15

Glu Ala Arg Lys Gln Gln Gln Pro Leu Ala Ser Phe Gln Asn Glu Val
                20                  25                  30

Gln Pro Ser Thr Arg His Phe Tyr Asp Ala Leu Gln Gly Ala Arg Thr
            35                  40                  45

Ala Phe Ile Leu Glu Cys Lys Lys Ala Gln Val Phe Gln Gly Val Ile
        50                  55                  60

Arg Asp Asp Phe Asp Pro Ala Arg Ile Ala Ala Ile Tyr Lys His Tyr
65                  70                  75                  80

Ala Ser Ala Ile Ser Val Leu Thr Asp Glu Lys Tyr Phe Gln Gly Ser
                85                  90                  95

Phe Asn Phe Leu Pro Ile Val Ser Gln Ile Ala Pro Gln Pro Ile Leu
            100                 105                 110

Cys Lys Asp Phe Ile Ile Asp Pro Tyr Gln Ile Tyr Leu Ala Arg Tyr
        115                 120                 125

Tyr Gln Ala Asp Ala Cys Leu Leu Met Leu Ser Val Leu Asp Asp Asp
    130                 135                 140

Gln Tyr Arg Gln Leu Ala Ala Val Ala His Ser Leu Glu Met Gly Val
145                 150                 155                 160

Leu Thr Glu Val Ser Asn Glu Glu Gln Glu Arg Ala Ile Ala Leu
                165                 170                 175

Gly Ala Lys Val Val Gly Ile Asn Asn Arg Asp Leu Arg Asp Leu Ser

```
                  180                 185                 190
Ile Asp Leu Asn Arg Thr Arg Glu Leu Ala Pro Lys Leu Gly His Asn
        195                 200                 205

Val Thr Val Ile Ser Glu Ser Gly Ile Asn Thr Tyr Ala Gln Val Arg
    210                 215                 220

Glu Leu Ser His Phe Ala Asn Gly Phe Leu Ile Gly Ser Ala Leu Met
225                 230                 235                 240

Ala His Asp Asp Leu His Ala Ala Val Arg Arg Val Leu Leu Gly Glu
                245                 250                 255

Asn Lys Val Cys Gly Leu Thr Arg Gly Gln Asp Ala Lys Ala Ala Tyr
                260                 265                 270

Asp Ala Gly Ala Ile Tyr Gly Gly Leu Ile Phe Val Ala Thr Ser Pro
                275                 280                 285

Arg Cys Val Asn Val Glu Gln Ala Gln Glu Val Met Ala Ala Ala Pro
                290                 295                 300

Leu Gln Tyr Val Gly Val Phe Arg Asn His Asp Ile Ala Asp Val Val
305                 310                 315                 320

Asp Lys Ala Lys Val Leu Ser Leu Ala Ala Val Gln Leu His Gly Asn
                325                 330                 335

Glu Glu Gln Leu Tyr Ile Asp Thr Leu Arg Glu Ala Leu Pro Ala His
                340                 345                 350

Val Ala Ile Trp Lys Ala Leu Ser Val Gly Glu Thr Leu Pro Ala Arg
                355                 360                 365

Glu Phe Gln His Val Asp Lys Tyr Val Leu Asp Asn Gly Gln Gly Gly
                370                 375                 380

Ser Gly Gln Arg Phe Asp Trp Ser Leu Leu Asn Gly Gln Ser Leu Gly
385                 390                 395                 400

Asn Val Leu Leu Ala Gly Gly Leu Gly Ala Asp Asn Cys Val Glu Ala
                405                 410                 415

Ala Gln Thr Gly Cys Ala Gly Leu Asp Phe Asn Ser Ala Val Glu Ser
                420                 425                 430

Gln Pro Gly Ile Lys Asp Ala Arg Leu Leu Ala Ser Val Phe Gln Thr
                435                 440                 445

Leu Arg Ala Tyr
                450
```

BIOTECHNOLOGICAL PRODUCTION OF L-TRYPTOPHAN

BACKGROUND OF THE INVENTION

Field of the Invention

The invention relates to the biotechnological production of tryptophan and derivatives thereof.

Description of the Related Art

L-tryptophan (L-trp) is a nutritionally essential amino acid widely used in food and pharmaceutical industry. L-trp can also serve as a key precursor for the biosynthesis of diverse biologically active secondary metabolites [1] and antitumor drugs such as violacein and deoxyviolacein [2-4], opening up new possibilities for the biosynthesis of high-value L-trp-based therapeutics. Currently, biotechnological processes, e.g. a microbial synthesis, are often used for producing L-trp on an industrial scale.

In microorganisms tryptophan is produced from chorismate, the end product of the shikimate pathway (shikimic acid pathway). From chorismate, tryptophan is biosynthesized via anthranilate (ANT), phosphoribosylanthranilate (PRA or PA), carboxyphenylamino-deoxyriboluse-5-phosphate (CdRP), indole-3-glycerol phosphate (IGP) and indole. The enzymes involved are anthranilate synthase (EC 4.1.3.27) encoded by the trpE gene, anthranilate phosphoribosyltransferase (EC 2.4.1.28) encoded by the trpD gene, phosphoribosylanthranilate isomerase (EC 5.3.1.24, PRAi) and indole-3-glycerol phosphate synthase (EC 4.1.1.48, IGPs) encoded by the trpC gene, and tryptophan synthase (EC 4.2.1.20) encoded by the trpB and trpA gene. The genes are clustered on the trp operon. TrpC (IGPs) has the activity of phosphoribosylanthranilate isomerase (PRAi) and indole-3-glycerol phosphate synthase (IGPs).

There have been several attempts in the prior art to improve microbial L-tryptophan synthesis. Overexpression of the entire trp operon did not increase productivity but only led to accumulation of anthranilate, the first intermediate in the metabolic chain (Lee K H et al [12]). EP 2803720 A2 suggests the partial overexpression of the trp operon, specifically, overexpression of trpD, trpC, trpB, and trpA, but not trpE. Another known approach is the expression of a yeast phosphoribosyl anthranilate transferase in E. coli (US 2016/0153014 A1).

There is still a need, however, to further improve the biotechnological L-tryptophan production. It is therefore an object of the invention to provide means for an enhanced microbial L-tryptophan synthesis.

BRIEF SUMMARY OF THE INVENTION

In a first aspect the invention provides a bacterial cell being genetically modified to express an indole-3-glycerol phosphate synthase, IGPs, the IGPs being less sensitive to inhibition by anthranilate compared to the wild type IGPs of the bacterial cell.

The invention is based on the surprising finding that microbial indole-3-glycerol phosphate synthase (IGPs), e.g. IGPs from *Escherichia coli* (EcIGPs or eIGPs), is sensitive to inhibition by anthranilate. Since anthranilate is an intermediate in the synthesis pathway from chorismate to L-tryptophan, which is synthesized before IGPs is involved, this type of inhibition will also be termed "feed-forward inhibition". The inventors have found that previous approaches for enhancing tryptophan productivity may have been unsuccessful or unsatisfactory because this feed-forward inhibition mechanism has not been considered before. The present invention, however, solves the problem by taking into account the negative regulation of IGPs by anthranilate. By using an IGPs or an enzyme having IGPs activity, which is less sensitive to inhibition by anthranilate than the wild-type enzyme of the bacterial cell, the tryptophan productivity can be considerably improved.

The term "heterologous" is used herein in its meaning known to those skilled in the art, and refers to the foreign origin of an element, for example an enzyme or other protein. "Foreign" means that the element thus does not occur in the target cell, and for example originates from a cell or an organism with different genetic makeup, such as an organism of a different species.

The term "homologous" is used herein with respect to an enzyme or protein to refer to it as a native enzyme or protein, i.e an enzyme or protein naturally occurring in the target cell, in contrast to a heterologous enzyme or protein.

By "expression" is meant here the conversion of a genetic information into a product, for example the formation of a protein or a nucleic acid on the basis of the genetic information. In particular, the term encompasses the biosynthesis of a protein based on genetic information including previous processes such as transcription, i.e. the formation of mRNA based on a DNA template.

The term "bacterial cell genetically modified to express an indole-3-glycerol phosphate synthase" relates to a bacterial cell, which is genetically engineered, such that an indole-3-glycerol phosphate synthase is expressed, i.e. produced, in the cell. The term "indole-3-glycerol phosphate synthase" (IGPs) relates to an enzyme having IGPs (EC 4.1.1.48) activity, i.e. the enzymatic activity of catalyzing the conversion of carboxyphenylamino-deoxyriboluse-5-phosphate (CdRP) to indole-3-glycerol phosphate (IGP). The term encompasses a bi- or multifunctional enzyme having, besides IGPs activity, one or more other activities, e.g. PRAi activity.

The term "less sensitive to inhibition by anthranilate" in relation to a first enzyme compared to a second enzyme means that the enzymatic activity of the first enzyme is higher than the enzymatic activity of the second enzyme in the presence of a given concentration of anthranilate and under similar conditions (e.g. temperature, pH, salt concentration etc.), in relation to the same enzymatically catalyzed reaction.

The term "mutated variant" in relation to a protein, e.g. an enzyme, relates to a protein or enzyme having a different amino acid sequence compared to the wildtype protein or enzyme. The term encompasses a protein having an altered amino acid sequence in comparison to the wildtype protein as a result of a mutation in the gene encoding the protein.

The term "heterologous enzyme having IGPs activity" relates to a heterologous enzyme having an enzymatic activity of an indole-3-glycerol phosphate synthase. The enzyme may also have one or more other enzymatic activities, e.g. phosphoribosylanthranilate isomerase (PRAi) activity or anthranilate synthase activity.

The term "anthranilate synthase II domain" or "AS II domain" relates to component II of the multifunctional enzyme anthranilate synthase comprising glutamine amidotransferase activity. Anthranilate synthase activity catalyzing the formation of anthranilate from chorismate could be provided by anthranilate synthase component I or component II. Component I uses ammonia rather than glutamine, whereas component II provides glutamine amidotransferase activity.

The term "anthranilate binding site" relates to a region of an enzyme, in particular an indole-3-glycerol phosphate synthase, where anthranilate (2-Aminobenzoic acid, CAS 118-92-3) molecules bind. In this context, the term "region" is not limited to a section of consecutive amino acids, but encompasses amino acid residues, which are in different positions in the enzyme, but get close to each other through spatial folding. The term "anthranilate binding site" encompasses amino acid residues that form temporary bonds with anthranilate. However, the term also encompasses amino acid residues neighboring amino acid residues that form temporary bonds with anthranilate. The term "neighboring" encompasses at least 3, preferably 2, most preferred 1 amino acid residues in the sequence to the left and/or right of the position of an amino acid residue forming a temporary bond with anthranilate. The term "anthranilate binding domain" is used synonymously to the term "anthranilate binding site".

In a preferred embodiment of the invention the bacterial cell of the invention is genetically modified to express
a) a mutated variant of a bacterial IGPs, the mutated IGPs variant being less sensitive to inhibition by anthranilate compared to the wild type IGPs of the bacterial cell, or
b) a heterologous enzyme having IGPs activity, the enzyme being less sensitive to inhibition by anthranilate compared to the wild type IGPs of the bacterial cell.

The inventors have found that bacterial IGPs has a anthranilate binding domain binding anthranilate with the result that the enzymatic conversion of phosphoribosylanthranilate (PRA or PA) via carboxyphenylamino-deoxyriboluse-5-phosphate (CdRP) to indole-3-glycerol phosphate (IGP) catalyzed by IGPs is noncompetetively inhibited by anthranilate, and that the bacterial IGPs can be engineered in order to make them less sensitive to inhibition by anthranilate. The invention thus provides mutated variants of a bacterial IGPs, the mutated IGPs variants being less sensitive to inhibition by anthranilate in comparison to the wild type IGPs of the bacterial cell.

In a preferred embodiment, the bacterial cell of the invention expresses a mutated variant of a bacterial IGPs, which is homologous to the genetically modified bacterial cell. Preferably, the genetically modified bacterial cell is an *E. coli* cell expressing a mutated variant of the *E. coli* IGPs.

Alternatively, the bacterial cell of the invention may be genetically modified to express a heterologous enzyme having IGPs activity, but being less sensitive to inhibition by anthranilate compared to the wild type IGPs of the bacterial cell. A heterologous enzyme may be of bacterial or other origin, e.g. form yeast. The inventors have found that some enzymes from non-bacterial species, e.g. from *Saccharomyces* or *Aspergillus* have IGPs activity, but are insensitive to anthranilate or even stimulated by anthranilate. In one embodiment of the invention, the bacterial cell of the invention is thus genetically modified in that it expresses such a heterologous enzyme having an IGPs activity, but being insensitive to and/or stimulated by anthranilate, e.g. an enzyme having an anthranilate synthase II domain, for example an enzyme from a *Saccharomyces* or *Aspergillus* species, especially preferred from *Saccharomyces cerevisiae* or *Aspergillus niger*.

In a further preferred embodiment the mutated variant of a bacterial IGPs has, compared to the wild-type bacterial IGPs, at least one amino acid replaced with a different amino acid in the anthranilate binding site of the bacterial IGPs, with the proviso that the mutated variant still has IGPs activity and is less sensitive to the inhibition by anthranilate in comparison to the non-mutated IGPs, i.e. the wild type IGPs.

In a further preferred embodiment of the invention the mutated variant of a bacterial IGPs has
a) alanine or glycine at position 60 instead of serine, and/or valine at position 8 instead of isoleucine, and/or phenylalanine at position 188 instead of leucine, or glutamine at position 58 instead of serine, valine at position 59 instead of proline, phenylalanine at position 60 instead of serine and glutamine at position 61 instead of lysine, compared to the sequence of SEQ ID NO: 1, or
b) the sequence of SEQ ID NO: 1, with the exception that at least one of the amino acids at positions 8 to 188 is replaced with a different amino acid, with the proviso that the mutated IGPs variant has IGPs activity and is less sensitive to inhibition by anthranilate compared to the wild type IGPs having the sequence of SEQ ID NO: 1.

In a preferred embodiment the mutated variant of a bacterial IGPs has the sequence of one of SEQ ID NO: 2 to SEQ ID NO: 5, or SEQ ID NO:30.

Preferably the genetically modified bacterial cell is an *Escherichia coli* cell.

The wild-type sequence of *E. coli* IGPs (EcTrpC) is presented in SEQ ID NO: 1. Mutated versions of *E. coli* IGPs are given in SEQ ID NO: 2 (I8V), SEQ ID NO: 3 (S60A), SEQ ID NO: 4 (S60G), SEQ ID NO: 5 (L188F) and SEQ ID NO: 30 (S58Q, P59V, S60F, K61Q). The wild-type sequence of ScTrpC is given in SEQ ID NO: 6, and the wild-type sequence of AgTrpC is given in SEQ ID NO: 7.

In a second aspect the invention also relates to an isolated or synthetic enzyme having the sequence of one of SEQ ID NO: 2 to SEQ ID NO: 5, or SEQ ID NO: 30.

In a third aspect the invention relates to a method for the biotechnological production of L-tryptophan, comprising the steps of growing a genetically modified bacterial cell according to the first aspect of the invention in a suitable growth medium in a bioreactor.

Preferably, the genetically modified bacterial used in the method of the invention is an *Escherichia coli* cell.

In a still further aspect the invention relates to the use of a bacterial cell according to the first aspect of the invention or an enzyme according to the second aspect of the invention, for the production of L-tryptophan, preferably for the production of L-tryptophan in an industrial scale in a bioreactor.

BRIEF DESCRIPTION OF THE SEVERAL VIEWS OF THE DRAWINGS

In the following, the invention will be described in further detail by way of example only with reference to the accompanying figures.

DETAILED DESCRIPTION OF THE INVENTION

Figure 1:
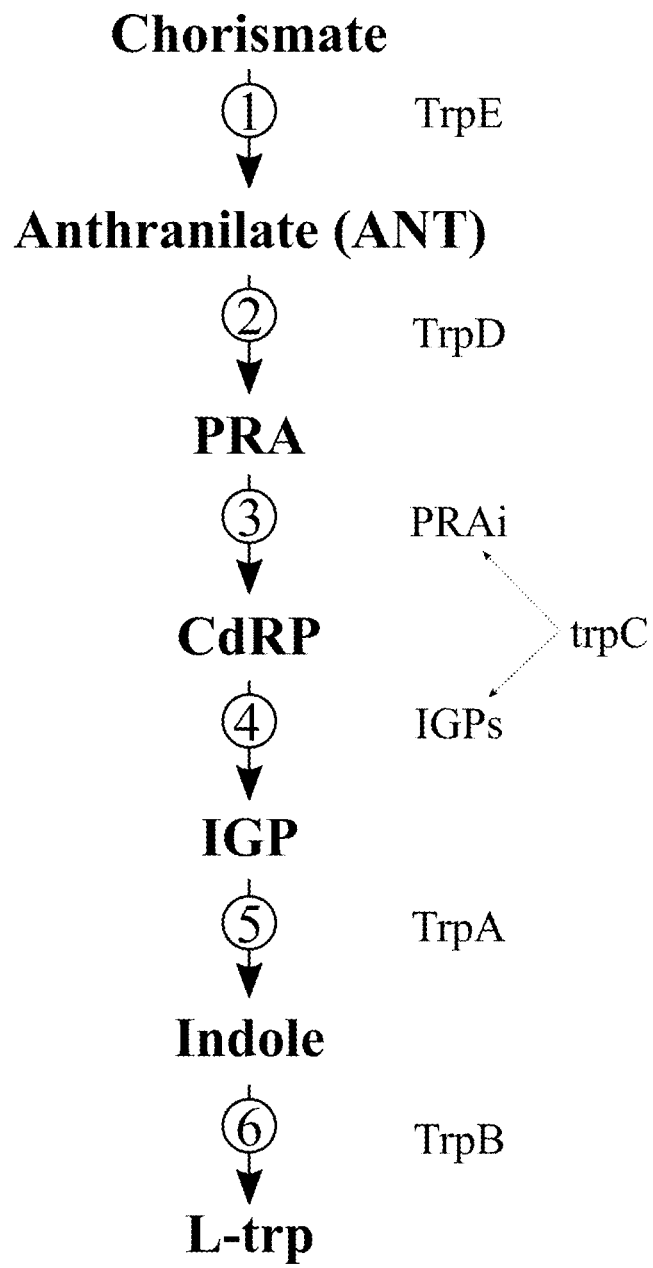
FIG. 1. Scheme of the biosynthesis of L-trp from chorismate in *E. coli*.

As shown in FIG. 1, L-trp is biosynthesized from chorismate, which is a common precursor for the biosynthesis of other two aromatic amino acids, namely L-phenylalanine (L-phe) and L-tyrosine (L-tyr). In Escherichia coli L-trp is biosynthesized from chorismate by the action of five enzyme encoded by the genes trpEDCBA organized as the trp operon. Previous studies showed that the trp operon is strictly regulated by feedback inhibition, repression, and attenuation through the end-product L-trp [7-10]. Biosynthesis of L-trp involves six reactions catalyzed by five enzymes: TrpE, TrpD, TrpC, TrpA, and TrpB. The bifunctional TrpC has phosphoribosylanthranilate isomerase (PRAi) and indole-3-glycerol phosphate synthase (IGPs) activity. Chorismate is first converted to anthranilate (ANT) by anthranilate synthase (EC 4.1.3.27) encoded by the trpE gene, which subsequently is converted to phosphoribosylanthranilate (PRA or PA) by anthranilate phosphoribosyltransferase (EC 2.4.1.28) encoded by the trpD gene. PRA is converted to carboxyphenylamino-deoxyriboluse-5-phosphate (CdRP) by phosphoribosylanthranilate isomerase (EC 5.3.1.24, PRAi) and CdRP is converted to indole-3-glycerol phosphate (IGP) by indole-3-glycerol phosphate synthase (EC 4.1.1.48, IGPs). Both reactions are catalyzed by the gene product of trpC. IGP is converted to Indole and subsequently to L-tryptophan by tryptophan synthase (EC 4.2.1.20) encoded by the trpB and trpA gene.

Plasmids and Strain Construction

The plasmids and strains used in this study are tabulated in Table 1.

TABLE 1

Plasmids and strains used in this study.

| Designation | Description | |
|---|---|---|
| Plasmids: | | |
| pTrc99A | Vector with trc promoter [20]ptrpE(S40F) | pTrc99A inserted with the trpES40F gene under the trc promoter |
| pET-eIGPs(WT) | pET22(b) vector inserted with the encoding gene for eIGPs-6His | |
| p6HTrpC | pTrc99A inserted with the encoding gene for 6His-TrpC | |
| p6HeIGPs | pTrc99A inserted with the encoding gene for 6His-eIGPs | |
| Strains: | | |
| S028 | An L-trp production strain [11]S028TC | The wildtype trpC gene replaced by the mutant trpCS60A in S028 |

The primers used in this study are listed in Table 2.

TABLE 2

| Primers | |
|---|---|
| Primers | Sequence |
| SmaI-trpE | ttgttcccgggtataaaggaggccatccatgcaaa cacaaaaaccgactc (SEQ ID NO: 8) |
| trpE-XbaI | gcagaatctagatcatcagaaagtctcctgtgcat g (SEQ ID NO: 9) |
| trpC-O1 | gcgctacagggtgcgcgcacggcgtttattctgga gtgcaagaaagcgtcgttgacagctagctcagtcc (SEQ ID NO: 10) |
| trpC-O2 | gatgccggattcgctgattaccgtcacgttgtgcc ccagtttcggcgcaaatttgatgcctgggcatgcg (SEQ ID NO: 11) |
| trpC-INF | atgcaaaccgtttagcgaa (SEQ ID NO: 12) |
| trpC-INR | caaatcgtcatgggccatca (SEQ ID NO: 13) |

TABLE 2-continued

Primers

| Primers | Sequence |
|---|---|
| NdeI-eIGPs | gcaacgcatatgcaaaccgttttagcgaaaatc gtcg (SEQ ID NO: 14) |
| eIGPs-XhoI | agtcgcctcgagtactttattctcacccagcaa cacc (SEQ ID NO: 15) |
| EcoRI-6H-trpC | cggcgcgaattcagaaggagatatacatatgcac caccaccaccaccaaaccgttttagcgaaaa tcgtcg (SEQ ID NO: 16) |
| trpC-XbaI | agcgtctctagacttaatatgcgcgcagcgt (SEQ ID NO: 17) |
| eIGPs-XbaI | agcgtctctagacttatactttattctcacc cagcaacacc (SEQ ID NO: 18) |

The tryptophan resistant gene trpES40F in the strain E. coli S028 (Table 1) was amplified with primers SmaI-trpE and TrpE-XbaI (Table 2) and subcloned into the vector pTrc99A (Table 1) at the sites SmaI and XbaI resulting in the plasmid ptrpE(S40F) (Table 1). The ORF of eIGPs (eIGPs, the IGPs in E. coli TrpC, EcTrpC) was isolated from the trpC gene in E. coli S028 with primers NdeI-eIGPs and eIGPs-XhoI (Table 2). It was then inserted into the vec-tor pET22 (b) at the sites NdeI and XhoI, generating the plasmid pET-eIGPs(wt). The theoretical peptide encoded by the isolated gene contains the first 259 residues of TrpC and a tag LGHHHHHH at the C-terminus for purification. The mutants of eIGPs were generated by using a typical pair of mutagenic primers (Table 2) to amplify the whole plasmid pET-eIGPs(WT). Those plasmids were named as pET-eIGPs (I8V), pET-eIGPs(I8A), pET-eIGPs(S60A), pET-eIGPs (S60G), pET-eIGPs(L188A), and pET-eIGPs(L188F), respectively. The plasmid p6HTrpC is constructed by inserting the PCR products amplified from E. coli S028 with primers EcoRI-6H-trpC and trpC-XbaI (Table 2) into the plasmid pTrc99A. The construction of the plasmid p6HeIGPs was done in the same way but with primers EcoRI-6H-trpC and eIGPs-XbaI (Table 2). As a result, the encoded proteins from the plasmid p6HTrpC and p6HeIGPs have 6His-tag at the N-terminus.

To construct the strain S028TC (Table 1), the approach based on selection/counterselection of markers for seamlessly chromosomal modification was implemented with the same procedure as reported previously by Lin et al [11]. The selection/counterselection marker cassette was amplified with primers trpC-01 and trpC-02 (Table 2) from the template plasmid pJLK [11]. The DNA fragment containing the mutation point (S60A) was amplified from the plasmid pET-eIGPs(S60A) with the primer pair trpC-INF/trpC-INR (Table 2). After recombination and selections, the final variant was confirmed by sequencing.

Cultivation Conditions

Batch fermentations were carried out in shake flasks. The seed medium and the fermentation medium are described in [11]. All batch fermentations were carried out at 37° C. and 250 rpm. An isolated colony was inoculated into 5 mL LB medium in the conical tube (50 mL) and grown overnight as preculture. The preculture was inoculated into 10 mL of seed medium in the baffled shake flask (100-mL) with the initial OD600=0.2. After grown for 8-10 hours, the seed culture was inoculated into 30 ml of fermentation medium in 300 mL baffled shake flasks to an initial OD600=0.1 in triplicate. After grown for 3 hours (OD600 was about 0.9), 0.2 mM IPTG was added into for induction. In all the cultivations, 100 µg/mL ampicillin was supplemented.

Docking Study

The complex of eIGPs with IGP was built up by duplicating the conformation of IGP from Mycobacterium tuberculosis IGPs (mIGPs or MtIGPs) to eIGPs with the computer program UCSF Chimera [21]. The research of flexible ligand docking to the rigid receptor was carried out with AutoDock Vina [22] integrated in Chimera.

Expression and Purification of eIGPs

The plasmids pET-eIGPs(wt) and those containing the mutant of eIGPs were transformed into the host E. coli BL21. The plasmids p6HTrpC and p6HeIGPs were transformed into the host E. coli Top10. Overnight cultures grown at 37° C. from isolated colonies were diluted 50-fold in 50 mL LB medium in shake flasks (300 mL). After grown at 37° C., 220 rpm to OD600 is about 0.6, inductions were started by adding 0.5 mM IPTG and then grown at 20° C., 220 rpm for 12-16 h. After cooling down on ice for 30 min, the cells were harvested by centrifugation at 4° C., 5000 rpm and washed once with 30 mL binding buffer (20 mM sodium phosphate, 500 mM NaCl, 20 mM imidazole, pH 7.4). The pellets were resuspended in 3 mL of binding buffer and disrupted through the multidirectional, simultaneous beating of specialized lysing matrix beads on them with the Fast-Prep®-24 instrument. The samples were then centrifuged at 4° C., 13000 rpm for 20 min. The targeted proteins were purified from the supernatants with prepacked His SpinTrap columns (GE Healthcare) with the user guide and eluted in 400 µl elution buffer (20 mM sodium phosphate, 500 mM NaCl, 500 mM imidazole, pH 7.4). The elution buffer was subsequently changed into the HEPPS buffer (50 mM HEPPS pH 7.5, 4 mM EDTA) for enzyme assay by using the Amicon® Ultra-0.5 Centrifugal Filter Devices at 4° C.

Enzymes Assay of IGPs

The activity of IGPs from E. coli was measured by monitoring the formation of IGP via absorbance at 278 nm [23] with a molar extinction coefficient value of 5500 $M^{-1}$ $cm^{-1}$ [24]. Assays were performed in 50 mM HEPPS pH 7.5, 4 mM EDTA at 30° C. with 20-25 µg/mL of purified enzymes in cuvettes. To investigate the effect of anthranilate on the activity of IGPs, the activities were measured in the presence of different concentrations of anthranilate. Unless stated otherwise, the reactions were started by adding 180 µM of the substrate CdRP. The synthesis of CdRP was performed by following the improved method reported by Kirschner et al. [24]. The concentration of the synthesized CdRP in the stock solution was determined by measuring the concentrations of the product IGP with completely converted reactions.

Analytical Methods

The quantification of glucose, 3-dehydroshikimate (DSA), and shikimate (SA) was determined by HPLC as reported in [25, 26]. The determination of L-trp was carried out by using a sensitive spectrophotometric method [27]. Other amino acids, ammonium, and anthranilate were quantified by HPLC after the derivatization with 6-Aminoquinolyl-N-Hydroxysuccinimidyl carbamate (Waters AccQ, Flour Reagent kit, USA) as reported by da Luz et al [25].

Structure-Based Studies of the Potential Anthranilate Binding Site in eIGPs

A series of crystal structures of IPGs have been solved, including the crystal structure of mIGPs in complex with the product IGP and anthranilate (PDB ID: 3T44), the complex of IGPs with IGP from Sulfolobus solfataricus (sIGPs, PDB ID: 1A53) [28], and E. coli TrpC (PDB ID: 1PII) [29]. The crystal structure of mIGPs in complex with the product IGP and anthranilate shows that the residues involved in the anthranilate binding site are located in a helix and three loops forming a 'gate' (see FIG. 13, 14). Anthranilate binds to IGPs and interacts with the product IGP by non-bonded contacts that may prevent the product IGP being released from the catalytic site. The secondary structures are quite conserved among the sequences of sIGPs, mIGPs, and eIGPs, although very much low identities were found among them (the identities between them are less than 30%). It was found that the residues involved in the binding site of anthranilate in mIGPs are 100% conserved in mIGPs and eIGPs (see FIG. 13). All three IGPs are (beta/alpha)8 barrel proteins, and almost all beta/alpha-structures are precisely aligned. Compared to eIGPs, one and two additional helices are inserted before the first beta strand of sIGPs and mIGPs, respectively. However, the active sites are highly conserved among them. The binding of anthranilate could make the product IGP bind more tightly at the active site because the indole ring of IGP is a little closer to the bottle of the barrel in mIGPs than in sIGPs (not shown).

To figure out whether there is a potential binding site of anthranilate in eIGPs, a docking study was carried out. The results showed that anthranilate can be docked into the complex of eIGPs with IGP. The top three docked anthranilates appear to be face to face with IGP (not shown). Whereas the benzoic rings of all the top five anthranilates docked to the complex of mIGPs with IGP, together with the reference one, are on the same surface which appears to be perpendicular to the surface of the indole group in IGP (not shown). Among them, the highest score of the docking results of anthranilate to mIGPs(IGP) and eIGPs(IGP) are 7.5 and 6.5, respectively. The comparable score may suggest a high probability that anthranilate can bind to eIGPs. Combined with the fact that the residues involved in binding anthranilate in mIGPs are 100% conserved in eIGPs and sIGPs, these results suggest that the anthranilate binding sites of eIGPs and mIGPs are the same. However, the configurations of the involved residues may be adjusted upon binding of anthranilate.

Anthranilate Noncompetitively Inhibits the Activity of eIGPs

Figure 2:
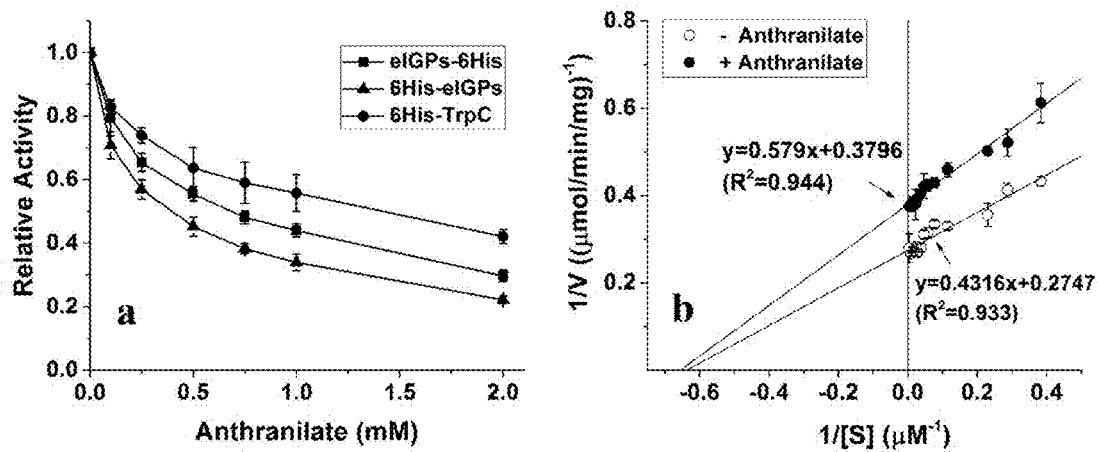
FIG. 2. Effect of anthranilate on eIGPS activity. Anthranilate inhibits eIGPS enzyme activity (a) and shows a noncompetitive inhibition of eIGPs (b).

To elucidate the effect of anthranilate on the enzyme activity of eIGPs, the catalytic activity of the isolated eIGPs (eIGPs-6His) was examined in the presence of different concentrations of anthranilate. The plot of the eIGPs activity against anthranilate showed that the activity was significantly decreased with the increase of anthranilate concentration (FIG. 2a). It was revealed that 46% of the activity of eIGPs can be inhibited by 0.5 mM anthranilate and more than 70% of activity is lost in the presence of 2 mM of anthranilate. The inhibition constant (IC50, 50% inhibitory concentration) of eIGPs-6His was measured to be about 0.70 mM.

E. coli TrpC has two distinct but covalently linked domains (the PRAi domain and the IGPs domain), each having distinguished activity catalyzing one of the reactions illustrated in FIG. 1. However, in many other organisms, IGPs exists as single chain enzyme [6]. Previous study showed that the PRAi domain may facilitate stabilizing the IGPs domain [30]. In order to figure out whether the PRAi domain has an influence on the inhibition resistance of eIGPs, the effect of anthranilate on the activity of IGPs in the form of eIGPs-PRAi (6His-TrpC) was tested. Considering the preciseness of the experiment, the isolated form 6His-eIGPs had been taken as a reference. The results show that the activity of eIGPs is notably inhibited by anthranilate either in the form of 6His-TrpC or in the form of 6His-eIGPs (FIG. 2a). The IC50 of 6His-eIGPs for anthranilate was estimated to be about 0.4 mM, while it is about 1.3 mM for 6His-TrpC. It can be concluded that the PRAi domain may assist the IGPs against the inhibition by anthranilate.

To identify the mechanism of the inhibition of eIGPs by anthranilate, the effect of the inhibitor on the Michaelis constants of eIGPs was investigated with 6His-TrpC. Various concentration of CdRP (from 2.6 to 260 μM) were used when the reactions carried out in the absence of anthranilate and in the presence of 0.5 mM anthranilate, respectively. The Lineweaver-Burk plot shows that the inhibitor anthranilate reduces the Vmax but almost has no effect on the Km (FIG. 2a). From the linear fit functions, the values of Vmax and Km were calculated to be 3.64 vs 2.63 μmol/min/mg and 1.57 vs 1.53 μM, respectively, with no anthranilate and with 0.5 mM of anthranilate. It suggests that anthranilate is a noncompetitive inhibitor of eIGPS. It is somewhat consistent with the fact that anthranilate has a distinguished binding site from the catalytic site based on the crystal structure analysis [19].

Mutational Analysis of the Anthranilate Binding Site of eIGPs

It was hypothesized that the observed failure to increase the production yield of L-trp by enhancing the trp operon [12] was caused by a feed-forward inhibition of IGPs due to accumulation of anthranilate. To test this hypothesis, the wild-type IGPs in the trp operon was replaced with an anthranilate-resistant mutant having mutations in the potential anthranilate binding site. To this end, structure-based approaches were used to guide the engineering of anthranilate-resistant IGPs. Since the N-terminal His-tag is too close to the binding site that somehow might affect the inhibition study as shown above as well as 6His-eIGPs has much poorer solubility than eIGPs-6His (data not show). All the mutational analysis was carried out based on eIGPs-6His.

The residues involved in the anthranilate binding site are highly conserved between eIGPs and mIGPs. A list of residues and the respective positions in eIGP and mIGP are given in Table 3.

TABLE 3

Figure 13:
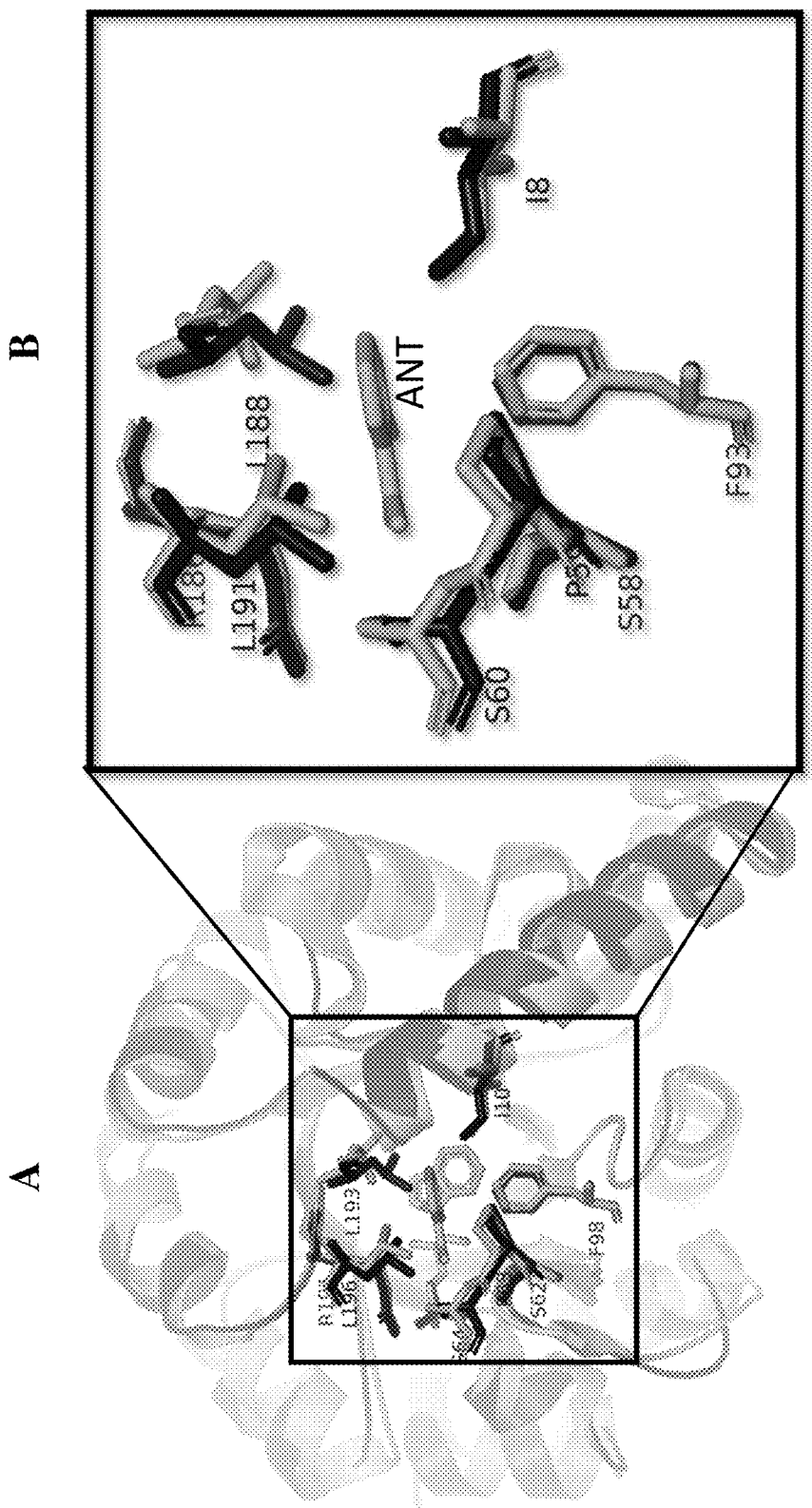
FIG. 13. A. Alignment of the crystal structures of indole glycerol phosphate synthase from Mycobacterium tuberculosis (PDB_ID: 3T44, light grey, MtIGPS or mIGPs) and of the enzyme from E. coli (PDB_ID: 1PII, black, EcIGPS or eIGPs). The residues (light grey sticks) involved in the anthranilate binding site of mIGPS are labeled. B. Alignment of the anthranilate binding sites of the indole glycerol phosphate synthase from Mycobacterium tuberculosis (light grey, mIGPs) and of the enzyme from E. coli (black, eIGPs). The residues (black sticks) involved in the anthranilate binding site of eIGPS are labeled. ANT=anthranilate.
Figure 14:
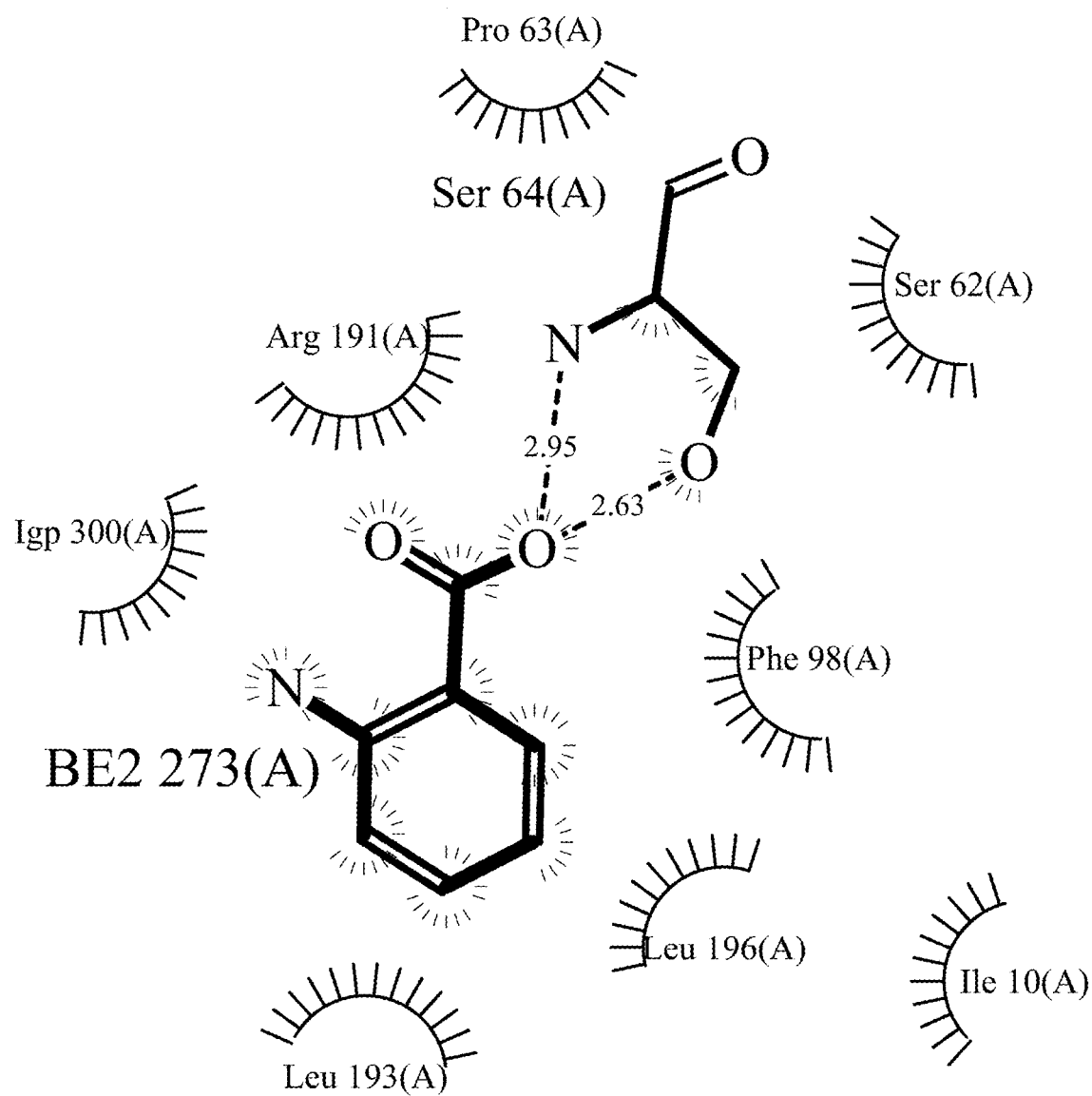
FIG. 14. Anthranilate binding site of mIGPs extracted from the crystal structure (PDB_ID: 3T44). Igp 300(A) and BE2 273(A) represent the product indole-3-glycerol phosphate of the enzyme IGPs and the ligand (or inhibitor) anthranilate, respectively. They are not residues and do not belong to the enzyme IGPs itself. Both are not involved in the anthranilate binding site.

Examples of conserved residues and their respective positions in the anthranilate binding sites of eIGPs and mIGPs (see FIGS. 13, 14).

| Amino acid | Position in eIGPs | Position in mIGPs |
| --- | --- | --- |
| I | 8 | 10 |
| S | 58 | 62 |
| P | 59 | 63 |
| S | 60 | 64 |
| F | 93 | 98 |
| R | 186 | 191 |
| L | 188 | 193 |
| L | 191 | 196 |

Among them, the three residues I8, S60, and L188 were chosen as candidates. A series of single point mutations based on these residues were generated by using non-complementary mutagenic primers (Table 4).

TABLE 4

Mutagenic primers.

| Primers | Sequence |
|---|---|
| eIGPs-I8X-F | gcagacaaggcgatttgggtag (SEQ ID NO: 19) |
| eIGPs-I8A-R | gacggctttcgctaaaacggtttgcat (SEQ ID NO: 20) |

TABLE 4-continued

Mutagenic primers.

| Primers | Sequence |
|---|---|
| eIGPs-I8V-R | gacgactttcgctaaaacggtttgcat (SEQ ID NO: 21) |
| eIGPs-S60A_F | gcaaaaggcgtgatccgtgat (SEQ ID NO: 22) |
| eIGPs-S60A_R | cggcgacgctttcttgcact (SEQ ID NO: 23) |
| eIGPs-S60G_F | tcgccgggaaaaggcgtgatccgtgatg (SEQ ID NO: 24) |
| eIGPs-S60G_R | cgctttcttgcactccaga (SEQ ID NO: 25) |
| eIGPs-L188A_R | atcgcggttgttgatgccaac (SEQ ID NO: 26) |
| eIGPs-L188A_F | gcgcgtgatttgtcgattga (SEQ ID NO: 27) |
| eIGPs-L188F_R | gttgttgatgccaacgacc (SEQ ID NO: 28) |
| eIGPs-L188F_F | cgcgattttcgtgatttgtcgattgatctc aacc (SEQ ID NO: 29) |

Figure 3:
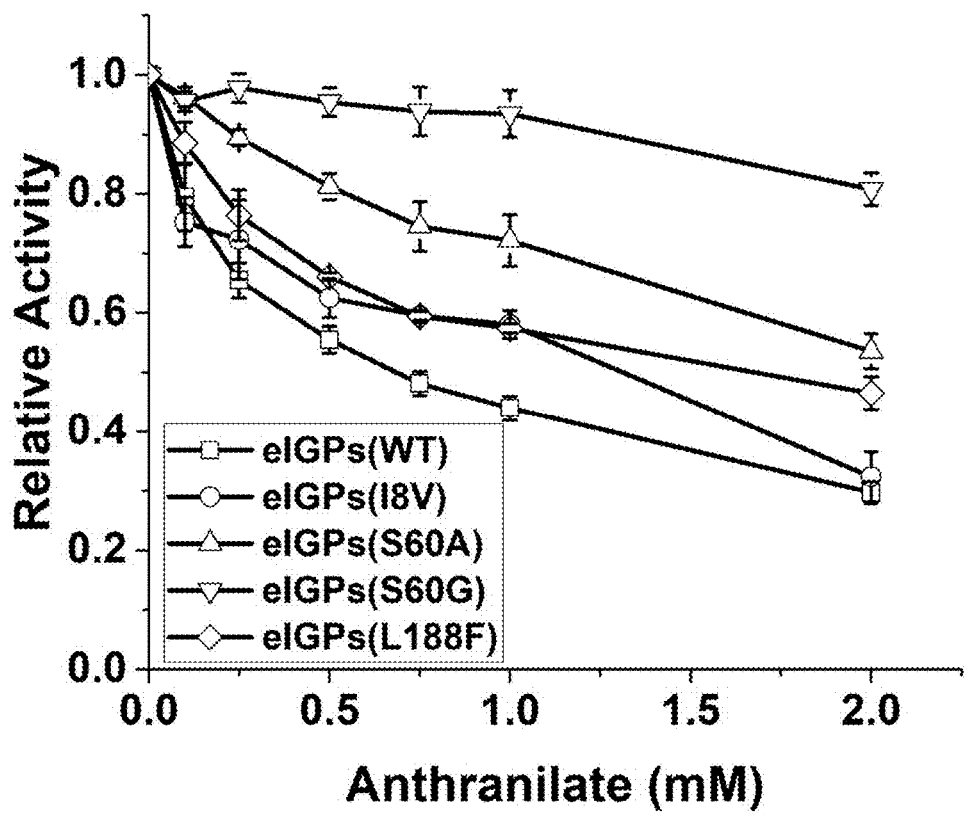
FIG. 3. Effects of anthranilate on the activities of the wild-type and mutant eIGPs.

SDS-PAGE analysis showed that all the mutants, especially I8V, have poorer solubility than the wild-type eIGPs (data not shown). The sensitivity of mutant I8A to anthranilate was significantly reduced but it has very low activity and solubility (data not show). While the mutant L188A has no detectable activity under the same condition. Therefore, the effect of anthranilate on the activity of this mutants was not investigated. Enzyme inhibition study on other mutants showed that all of them are less sensitive to anthranilate than the wild-type eIGPs (FIG. 3). Among them, the anthranilate resistance of the mutants I8V and L188F were slightly increased while it was significantly improved for the mutants S60A and S60G. In the presence of 2 mM of anthranilate, only 20% and 46% of the activities of the mutants S60G and S60A were inhibited while 70% of activity of the wild type was lost (data not shown). The IC50 of mutant S60A was measured to be about 2.0 mM, which is about 3 times as much as that of the wild-type eIGPs. These results suggest that the residues I8, S60, and L188 are involving in the potential binding site of anthranilate of eIGPs.

Among these mutants, S60A has the highest specific activity, but it is lower than that of the wild type in the absence of anthranilate (Table 5).

TABLE 5

Specific activities of wild-type and mutant eIGPs. The concentration of CdRP was determined from the converted IGP with a molar extinction coefficient value of 5500 $M^{-1}$ $cm^{-1}$ [24]. The data are presented as average value ± standard deviation, — enzyme assays were not carried out.

| | Specific activity (μmol/min/mg) in the absence of anthranilate. | | | | |
|---|---|---|---|---|---|
| CdRP/μM | WT | I8V | S60A | S60G | L188F |
| 180 | 2.46 ± 0.09 | 0.90 ± 0.03 | 2.13 ± 0.01 | 1.92 ± 0.02 | 1.04 ± 0.02 |
| 60 | 2.54 ± 0.11 | — | 2.05 ± 0.06 | 1.75 ± 0.03 | — |
| 18 | 2.17 ± 0.03 | — | 1.60 ± 0.03 | 1.13 ± 0.02 | — |

The specific activities of both S60A and S60G were higher than that of the wild type in the presence of more than 0.1 mM of anthranilate and with 180 μM of CdRP. It was reported that the efficiency (Kcat/Km) of the mutant S60A was only about 30% of that of the wild-type enzyme in the two-domain form due to the decreased affinity of the substrate [31]. The lower catalytic efficiency was also found in the single-domain form as shown in Table 5. In the presence of 18 μM CdRP and in the absence of anthranilate, the activities of the mutants S60A and S60G are only 74 and 52% of that of the wild-type enzyme (data not shown). The rates of increased absorbance (data not shown) suggested that S60G held the largest Km among these three enzymes.

Impact of Anthranilate-Resistant eIGPs on L-Trp Production

Figure 4:
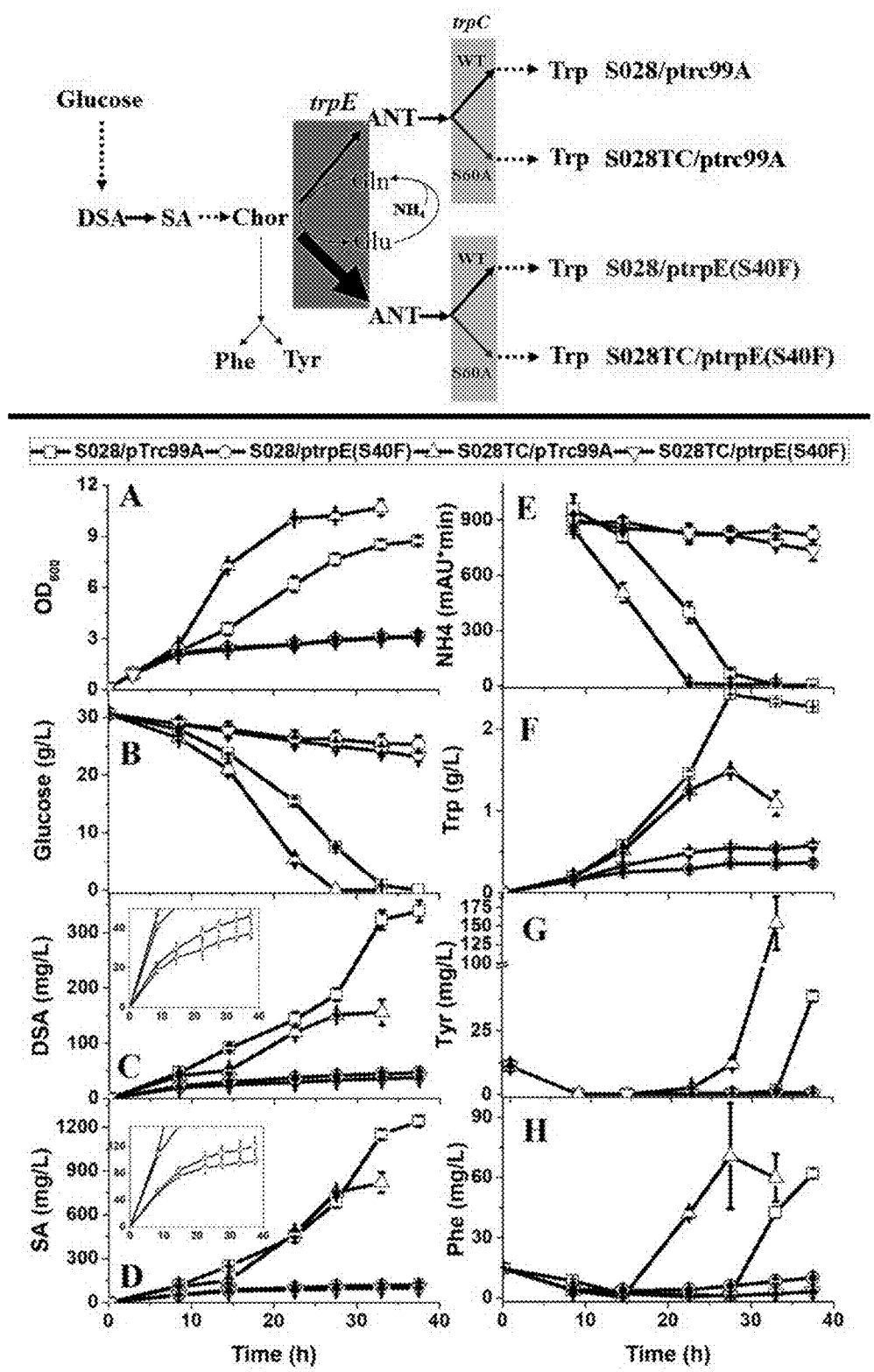
FIG. 4. The gene types (top) and the fermentation results (bottom) of the four strains S028/ptrpE(S40F), S028TC/ptrpE(S40F), S028/ptrc99A, and S028TC/ptrc99A. (a) Growth, (b) glucose consumption, (c) accumulation of dehydroshikimate (DSA), (d) accumulation of shikimate (SA), (e) ammonium ion consumption, (f) L-trp production, (g) L-tyr formation, and (h) L-phe formation. The induction was carried out at 3 h of the fermentation time by adding 0.2 mM IPTG FIG. 5a L-trp production of the strain S028TC/ptrpE (S40F) higher than that of the reference strain.

In order to demonstrate the inhibition of eIGPs by anthranilate in vivo and to explore whether an anthranilate-resistant eIGPs is better for L-trp production as anthranilate is accumulated, it's necessary to construct a recombinant strain containing anthranilate-resistant eIGPs. As presented above, the mutant S60A has the highest catalytic efficiency among the mutants. It also has significantly reduced sensitivity to anthranilate compared to the wild-type eIGPs. Therefore, we replaced the wild-type gene trpC in the strain S028 with the mutant gene trpCS60A, resulting in the recombinant strain S028TC (Table 1). To accumulate anthranilate intracellularly to the level which could significantly inhibit the activity of IGPs, the first reaction of the trp operon, which converts chorismate to form anthranilate, requires to be enhanced. To this end, the availability of the feedback-inhibition-resistant anthranilate synthase (TrpES40F) was increased by overexpressing the gene trpES40F with the plasmid ptrpE(S40F) (Table 1). The plasmid ptrpE(S40F) was introduced into the strains S028 and S028TC, generating the strains S028/ptrpE(S40F) and S028TC/ptrpE(S40F). In the meanwhile, the reference strains S028/ptrc99A and S028TC/ptrc99A were constructed by introducing the blank vector ptrc99A into the hosts. The differences between these four strains were illustrated in FIG. 4.

As shown in FIG. 4a, the strain S028TC/ptrc99A, containing the mutant TrpCS60A which has a lower IGPs activity than that of the wild-type TrpC contained in the strain S028/ptrc99A, showed a higher growth rate and obtained a higher production of biomass. It seemed that the higher growth rate reasonably resulted in the higher glucose consumption rate, however, it reduced the metabolic flux for biosynthesis of L-trp. During the fermentation time from 8.5 to 27.5 h, the glucose consumption rates for the strains S028/ptrc99A and S028TC/ptrc99A were calculated to be 1.06 ($R2=0.9764$) and 1.47 g/L/h ($R2=0.9807$), respectively (FIG. 4b). For both of them, the intermediates DSA (FIG. 4c) and SA (FIG. 4d) were notably accumulated during the fermentations. Although the accumulation of the intermediates in the strain S028/ptrc99A was higher than that in the strain S028TC/ptrc99A, the maximal L-trp production of the former strain was much higher (about 1.7 times) than that of the latter one (FIG. 4f). Meanwhile, the strain S028/ptrc99A produced fewer byproducts Tyr (FIG. 4g) and Phe (FIG. 4h) compared to the strain S028TC/ptrc99A. At the end of the fermentation, the sum of all the measurable intermediates (DSA and SA), byproducts (Tyr and Phe) and L-trp for the strain S028/ptrc99A was about 20 mM, while it was about 12 mM for the strain S028TC/ptrc99A. This difference indicated that less metabolic flux was redirected into the chorismate pathway while more metabolic flux was used for cell growth caused by the seriously reduced catalytic efficiency of IGPs in the L-trp branch pathway. It indicated that higher activity of IGPs is essential for achieving higher efficiency of trp operon.

It is notable that nitrogen was exhausted earlier than glucose during the fermentation (FIGS. 4b and 4e). And it seems that the L-trp production was limited by nitrogen supply when glucose was not a limitation yet. As shown in 4e, f, g, and h, the nitrogen limitation could stop the L-trp production and trigger the accumulation of the byproducts (Phe and Tyr). NH4 is required for biosynthesis of L-gln which is a substrate for L-trp production. The shortage of NH4 can, therefore, stop the reaction which converts chorismate into the L-trp branch pathway. As a result, the availability of chorismate was increased for biosynthesis of Phe and Tyr. From this point of view, the L-trp production and yield would be improved if the shortage of nitrogen was eliminated. Thus, it is necessary to add more nitrogen source in the newly designed fermentation medium.

Interestingly, it was found that the cell growth was significantly inhibited when the gene trpES40F was overexpressed either in S028 or S028TC, but the reason is unclear. As a result, the glucose consumption rates, as well as the accumulation of the intermediates (DSA and SA) for these two strains were relatively low (FIGS. 4a, b, c and d).

Figure 5:
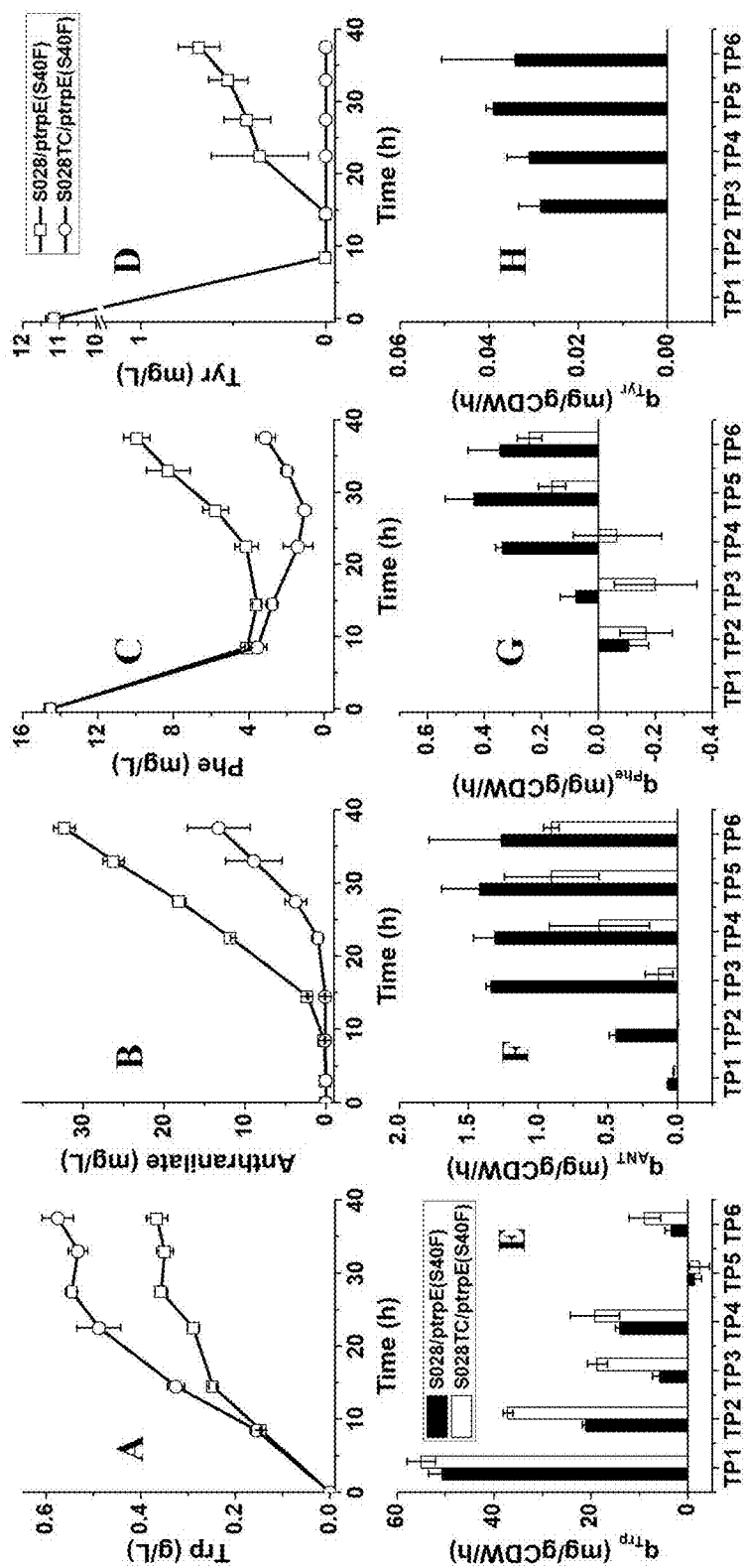
FIG. 5b Intermediate anthranilate accumulation as a result of the overexpression of the gene trpES40F vs. reference strain.
FIG. 5c Higher concentrations of the byproduct Phe produced by the reference strain.
FIG. 5d Higher concentrations of the byproduct Tyr produced by the reference strain.
FIG. 5e The specific production rate of L-trp (qTrp) for both strains kept decreasing.
FIG. 5f The specific formation rate of anthranilate kept increasing rapidly after the induction until stabilization.
FIG. 5g The specific formation rate of Phe kept increasing rapidly after the induction until stabilization.
FIG. 5h the specific formation rate of Tyr kept increasing rapidly after the induction until stabilization.

As shown in FIG. 5a, L-trp production of the strain S028TC/ptrpE(S40F) was much higher than that of the reference strain S028/ptrpE(S40F). It seems that both strains almost stopped producing L-trp after 27.5 h, but the L-trp production (575±33 mg/L) of the strain S028TC/ptrpE (S40F) was significantly higher (57%) than that (366±22 mg/L) of the reference strain at the end of fermentation (37.5 h). As expected, intermediate anthranilate was accumulated as a result of the overexpression of the gene trpES40F but it was much serious in the reference strain (FIG. 5b). Not like L-trp, the accumulation of anthranilate kept constantly increasing after the induction. At the end of fermentation, the accumulated anthranilate in the reference strain reached 32.3±1.3 mg/L, which is 1.4 times higher than that (13.2±3.9 mg/L) of the strain S028TC/ptrpE(S40F). Similarly, much higher concentrations of the byproducts Phe (FIG. 5c) and Tyr (FIG. 5d) were also produced by the reference strain.

Note that the specific production rates of L-trp (qTrp) for both strains kept decreasing while the specific formation rates of anthranilate, Phe, and Tyr kept increasing rapidly after the induction and became, somehow, stable after that. However, the qTrp of the strain S028TC/ptrpE(S40F), which expressed the mutant TrpC(S60A) less sensitive to anthranilate, was higher than that of the reference strain. Since the strain S028/ptrpE(S40F) and S028TC/ptrpE(S40F) showed almost the same growth curve (FIG. 4a), it was assumed that the substrates involved in the L-trp branch and derived from other pathways were supplied in nearly the same amount. Combined with the fact that the activity of eIGPs is inhibited by anthranilate in vitro, these results suggested the inhibition can happen in vivo too. The phenomenon that the increased accumulation of anthranilate, Phe, and Tyr with the stable production of L-trp implied that the activities of IGPs in both strains may be significantly inhibited after 27.5 h.

Figure 6:
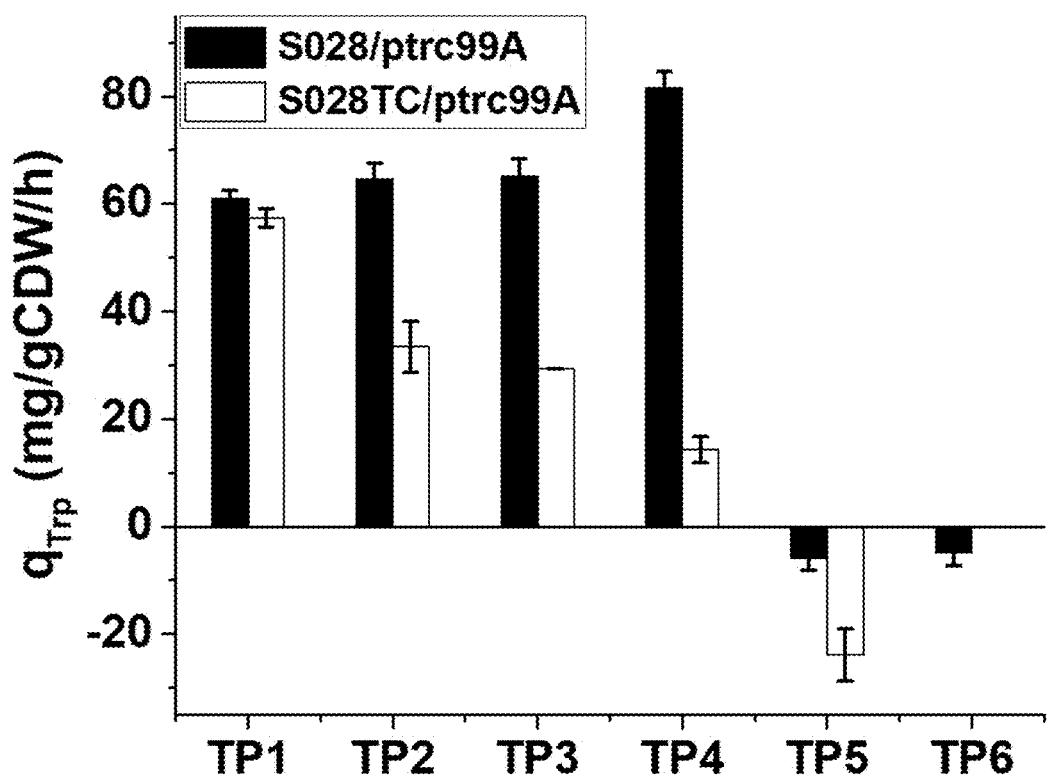
FIG. 6. The specific production rates of L-trp of the strains S028/ptrc99A (black bar) and S028TC/ptrc99A (white bar) during the batch fermentation in shake flasks. See FIG. 5 for TP1 to TP6.

As shown in FIG. 6, the qTrp of the strain S028/ptrc99A was not decreased after the induction when there was no limitation of nitrogen and glucose. While the qTrp of the strain S028TC/ptrc99A was decreased during the fermentation time TP2 (from 8.5 to 14.5 h) when nitrogen and glucose were sufficiently supplied. These indicated that the intracellular concentration of anthranilate in the strain S028/ptrc99A did not reach to the level which can significantly inhibit the activity of IGPs. However, in the strain S028TC/ptrc99A, it may get to the level which can inhibit the IGPs notably, although there was no extracellular anthranilate detected in four-time diluted samples during the fermentation.

The above described structural studies and docking results showed that anthranilate is able to bind to eIGPs. It was shown by the enzyme assay that anthranilate feed-forward inhibits the enzyme activity of eIGPs in a noncompetitive manner. A mutational study of the anthranilate binding site of eIGPs for three of the residues involved (18, S60, and L188) showed that single point mutants, especially S60A and S60G, resulted in significantly reduced anthranilate sensitivity. However, all of the mutations of these residues led to a dramatical decline in the enzyme catalytic efficiency. In vivo study showed that the partially anthranilate-resistant mutant of IGPs, S60A, even though it has lower catalytic efficiency, is much more beneficial for producing L-trp than the wild type IGPs when anthranilate is accumulated during the fermentation.

Figure 7:
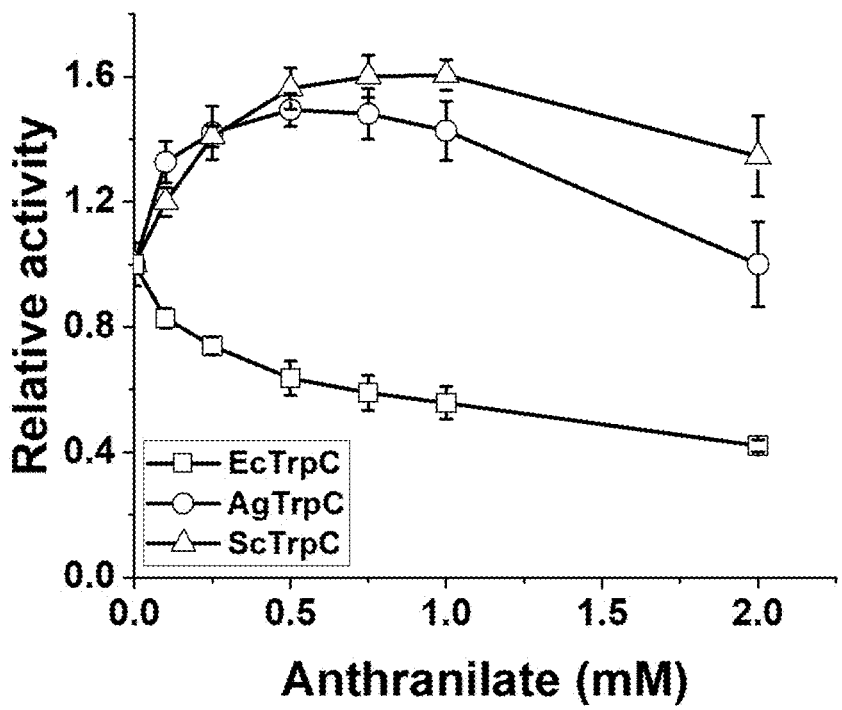
FIG. 7. Feed-forward regulation of the activity of indole glycerol phosphate synthase in TrpC by anthranilate. EcTrpC, TrpC from E. coli, is subjected to negative feed-forward regulation by anthranilate while ScTrpC and AgTrpC, TrpC from Saccharomyces cerevisiae and Aspergillus niger, respectively, are positively regulated by anthranilate.
Figure 8:
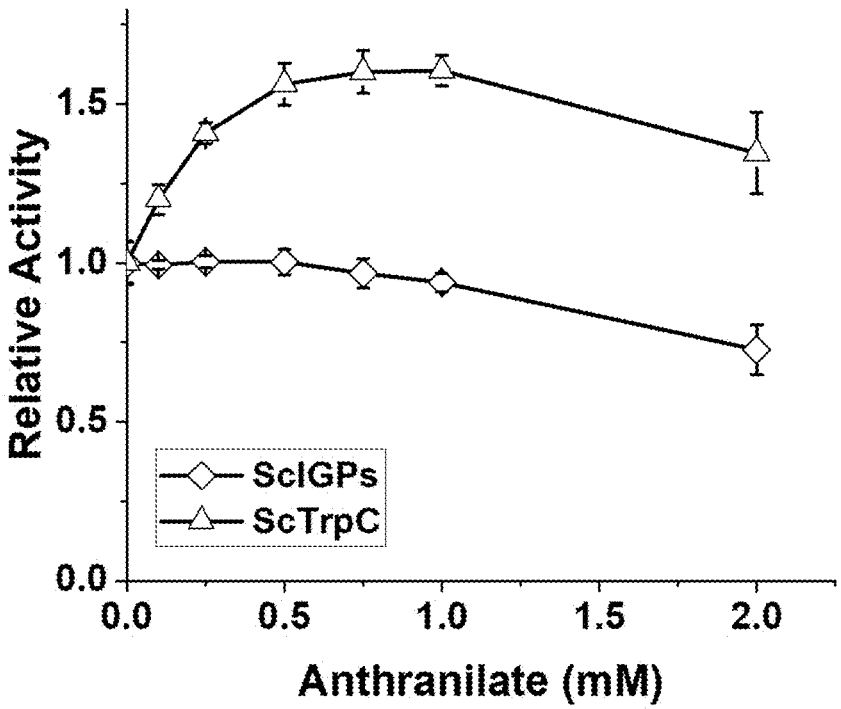
FIG. 8. Effects of anthranilate on the activities of ScTrpC and ScIGPs (ScIGPs=ScTrpC without anthranilate synthase II domain).

Fungal IGPs Having a Anthranilate Synthase II Domain are not Inhibited by Anthranilate As shown in FIG. 7, TrpC from *Saccharomyces cerevisiae* and *Aspergillus niger*, ScTrpC and AgTrpC are activated by anthranilate. Structural analysis show that the positively regulated TrpC (ScTrpC and AgTrpC) contain the anthranilate synthase II domain (AS II domain) while the negatively regulated *E. coli* TrpC (EcTrpC) do not contain this domain. After removing the anthranilate synthase II domain from ScTrpC, no activation was observed for the resulting ScIGPs (FIG. 8). This suggest that the anthranilate synthase II domain is essential for possessing the positive regulation.

Impact of Anthranilate-Activated TrpC on L-Trp Production

To investigate the effect of anthranilate-activated TrpC on L-trp production, a trpC defective strain S092 was generated by deleting the trpC gene from tryptophan producing strain S028. Then, EcTrpC, ScTrpC, and AgTrpC were introduced into 5092, respectively, in order to obtain recombinant strains S092/pEcTrpC, S092/pScTrpC, and S092/pAgTrpC.

Figure 9:
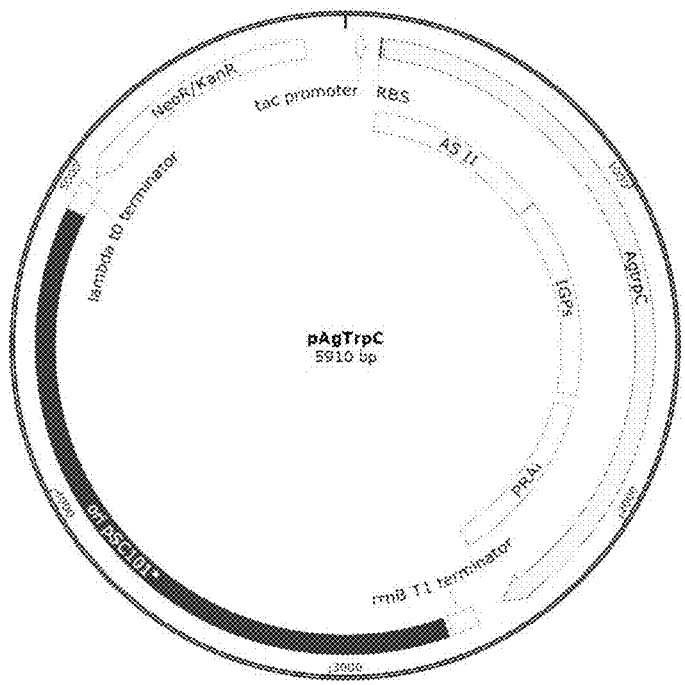
FIG. 9 Map of plasmid pAgTrpC.
Figure 10:
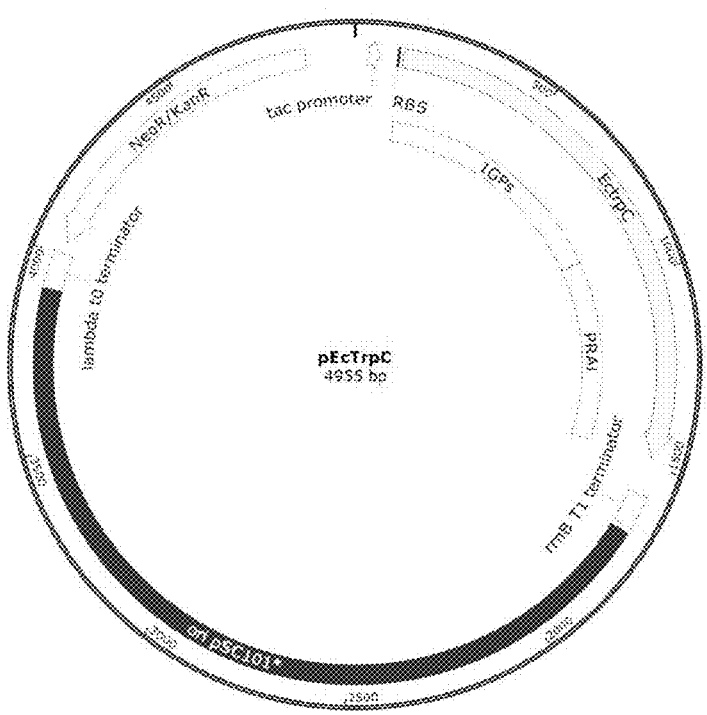
FIG. 10 Map of plasmid pEcTrpC.
Figure 11:
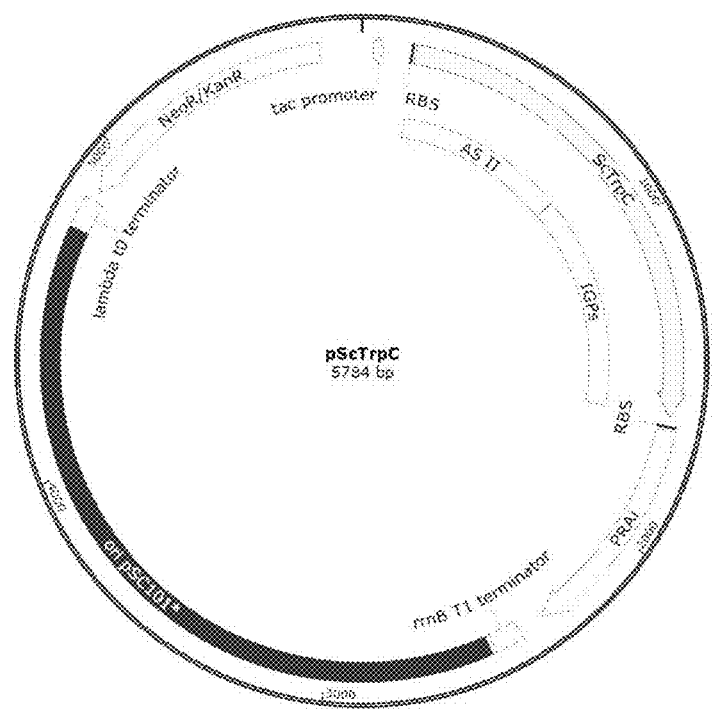
FIG. 11 Map of plasmid pScTrpc.

Plasmids used are shown in FIGS. 9 to 11. Batch fermentations were performed with these three strains in a bioreactor. As summarized in Table 6, both the strains S092/pScTrpC and S092/pAgTrpC have higher tryptophan production and yield than the control strain S092/pEcTrpC. These results suggest anthranilate-activated TrpC benefits tryptophan production.

TABLE 6

Comparison of tryptophan productivity between the strains having the EcTrpC, ScTrpC and AgTrpC.

| Strain | Glucose consumed (g) | Trp produced (g) | Yield (g/g) |
|---|---|---|---|
| S092/pEcTrpC#1 | 16.15 | 1.07 | 0.067 |
| S092/pEcTrpC#2 | 15.60 | 1.16 | 0.074 |
| S092/pScTrpC | 14.60 | 1.56 | 0.107 |
| S092/pAgTrpC | 15.50 | 1.63 | 0.105 |

Impact of Multiple Mutations in E. coli IGPs

In further studies multiple mutations were induced at positions 58-61 in E. coli IGPs. The positions relate to the wildtype sequence in SEQ ID NO: 1. Mutant strains 5092::TrpSen::pIBB24-trpC$^{S58Q\text{-}P59V\text{-}S60F\text{-}K61Q}$ (having glutamine at position 58 instead of serine, valine at position 59 instead of proline, phenylalanine at position 60 instead of serine and glutamine at position 61 instead of lysine, SEQ ID NO: 30) and 5092::TrpSen::pIBB24-trpC$^{S58Q\text{-}P59L\text{-}S60R\text{-}K61C}$ (having glutamine at position 58 instead of serine, leucine at position 59 instead of proline, arginine at position 60 instead of serine and cysteine at position 61 instead of lysine) were produced and compared to the strain S092::TrpSen::pIBB24-trpC$^{SPSK}$, expressing EcIGPs having the wildtype sequence serine-proline-serine-lysine at positions 58-61.

Fermentation results are shown in Table 7 below.

TABLE 7

Comparison of fermentation results with E. coli strains containing the EctrpC$^{SPSK}$ (Trp CWT), EctrpC$^{S58Q\text{-}P59V\text{-}S60F\text{-}K61Q}$ (TrpC QVFQ), and EctrpC$^{S58Q\text{-}P59L\text{-}S60R\text{-}K61C}$ (TrpC qLRC) variants grown on F-II by shake flask at 20 hours. DCW = dry cell weight; con. = concentration; qtrp = specific production rate (mg Trp per g DCW and hour).

| Strain | DCW (g/L) | L-Trp con. (mg/L) | qtrp (mg/gDCW/h) |
|---|---|---|---|
| S092::trpSen::TrpC WT | 0.78 | 1042.5 | 53.59 |
| S092::trpSen::TrpC QLRC | 0.36 | 96.27 | 10.82 |
| S092::trpSen::TrpC QVFQ | 0.96 | 1214.73 | 50.72 |

The mutant having a sequence of QVFQ at positions 58-61 grew to a higher density and produced more tryptophan in terms of absolute yield.

Figure 12:
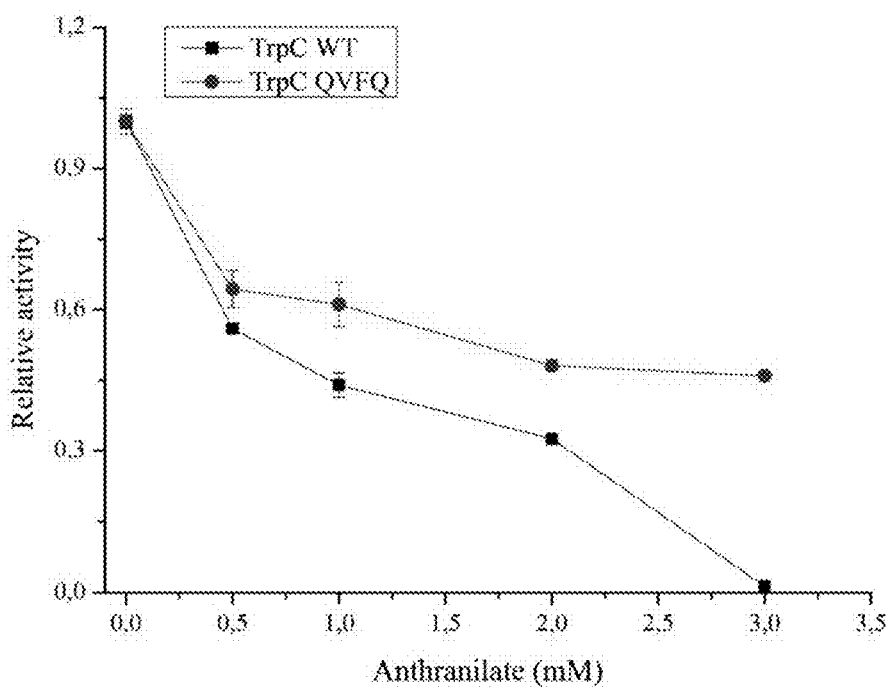
FIG. 12. Effect of anthranilate on the activities of EcTrpC WT and TrpC QVFQ.

The determination of the specific activities TrpCs in the presence of increasing anthranilate concentrations showed that the QVFQ variant was significantly less inhibited by anthranilate compared to the wildtype TrpC, as shown in Table 8 below (see also FIG. 12).

TABLE 8

Specific activities of the TrpC WT and TrpC QVFQ.

| Anthranilate (mM) | Specific activities (µmol/min/mg) | |
|---|---|---|
| | WT | QVFQ |
| 0 | 2.203 ± 0.143 | 1.886 ± 0.067 |
| 0.5 | 1.233 ± 0.003 | 1.124 ± 0.074 |

TABLE 8-continued

Specific activities of the TrpC WT and TrpC QVFQ.

| Anthranilate (mM) | Specific activities (µmol/min/mg) | |
|---|---|---|
| | WT | QVFQ |
| 1 | 0.968 ± 0.056 | 1.152 ± 0.089 |
| 2 | 0.717 ± 0.017 | 0.906 ± 0.022 |
| 3 | 0.028 ± 0.005 | 0.866 ± 0.016 |

Apparent kinetic constants of wildtype and QVFQ variant are presented in Table 9.

TABLE 9

Apparent kinetic constants of wildtype and QVFQ TrpC variant

| | CdRP | | |
|---|---|---|---|
| Enzyme | km (µM) | kcat (s$^{-1}$) | kcat/km (M$^{-1s-1}$) |
| WT | 8.370 ± 0.150 | 0.036 ± 0.002 | 430.108 |
| QVFQ | 6.140 ± 0.040 | 0.027 ± 0.001 | 439.740 |

REFERENCES

1. Wunsch C, Mundt K, Li S-M (2015) Targeted production of secondary metabolites by coexpression of non-ribosomal peptide synthetase and prenyltransferase genes in Aspergillus. Appl Microbiol Biotechnol 99(10): 4213-4223. doi: 10.1007/s00253-015-6490-8
2. Fang M-Y, Zhang C, Yang S et al. (2015) High crude violacein production from glucose by Escherichia coli engineered with interactive control of tryptophan pathway and violacein biosynthetic pathway. Microb. Cell Fact. 14: 8. doi: 10.1186/s12934-015-0192-x
3. Fang M, Wang T, Zhang C et al. (2016) Intermediate-sensor assisted push-pull strategy and its application in heterologous deoxyviolacein production in Escherichia coli. Metab Eng 33: 41-51. doi: 10.1016/j.ymben.2015.10.006
4. Rodrigues A L, Trachtmann N, Becker J et al. (2013) Systems metabolic engineering of Escherichia coli for production of the antitumor drugs violacein and deoxyviolacein. Metab. Eng. 20: 29-41
6. Merino E, Jensen R A, Yanofsky C (2008) Evolution of bacterial trp operons and their regulation. Curr Opin Microbiol 11(2): 78-86. doi: 10.1016/j.mib.2008.02.005
7. Bertrand K, Yanofsky C (1976) Regulation of Transcription Termination in Leader Region of Tryptophan Operon of Escherichia-Coli Involves Tryptophan or Its Metabolic Product. J. Mol. Biol. 103(2): 339-349

8. Kwak J H, Hong K W, Lee S H et al. (1999) Identification of amino acid residues involved in feedback inhibition of the anthranilate synthase in *Escherichia coli*. J. Biochem. Mol. Biol. 32(1): 20-24
9. Platt T (1981) Termination of Transcription and Its Regulation in the Tryptophan Operon of *Escherichia-Coli*. Cell 24(1): 10-23
10. Zurawski G, Elseviers D, Stauffer G V et al. (1978) Translational control of transcription termination at the attenuator of the *Escherichia coli* tryptophan operon. Proc. Natl. Acad. Sci. U.S.A. 75(12): 5988-5992
11. Chen L, Zeng A-P (2017) Rational design and metabolic analysis of *Escherichia coli* for effective production of L-tryptophan at high concentration. Appl Microbiol Biotechnol 101(2): 559-568. doi: 10.1007/s00253-016-7772-5
12. Lee K H, Park H M, Lee H H et al. (2014) Microorganisms of *Escherichia coli* having enhanced L-tryptophan production and method for producing L-tryptophan by using same (EP2803720)
19. Reddy M, Bruning J B, Thurman C et al. (2012) Crystal structure of *Mycobacterium* tuberculosis Indole Glycerol Phosphate Synthase (IGPS) in complex with indole glycerol phosphate (IGP) amd anthranilate. doi: 10.2210/pdb3t44/pdb
20. Amann E, Ochs B, Abel K J (1988) Tightly regulated tac promoter vectors useful for the expression of unfused and fused proteins in *Escherichia coli*. Gene 69(2): 301-315
21. Pettersen E F, Goddard T D, Huang C C et al. (2004) UCSF Chimera—a visualization system for exploratory research and analysis. J Comput Chem 25(13): 1605-1612. doi: 10.1002/jcc.20084
22. Trott O, Olson A J (2010) AutoDock Vina: improving the speed and accuracy of docking with a new scoring function, efficient optimization, and multithreading. J Comput Chem 31(2): 455-461. doi: 10.1002/jcc.21334
23. Zaccardi M J, Mannweiler O, Boehr D D (2012) Differences in the catalytic mechanisms of mesophilic and thermophilic indole-3-glycerol phosphate synthase enzymes at their adaptive temperatures. Biochem. Biophys. Res. Commun. 418(2): 324-329. doi: 10.1016/j.bbrc.2012.01.020
24. Kirschner K, Szadkowski H, Jardetzky T S et al. (1987) Phosphoribosylanthranilate isomerase-indoleglycerolphosphate synthase from *Escherichia coli*. In: Metabolism of Aromatic Amino Acids and Amines, vol 142. Academic Press, pp 386-397
25. da Luz J A, Hans E, Zeng A-P (2014) Automated fast filtration and on-filter quenching improve the intracellular metabolite analysis of microorganisms. Eng. Life Sci. 14(2): 135-142. doi: 10.1002/elsc.201300099
26. Rajesh Reddy Bommareddy, Zhen Chen, Sugima Rappert et al. (2014) A de novo NADPH generation pathway for improving lysine production of *Corynebacterium glutamicum* by rational design of the coenzyme specificity of glyceraldehyde 3-phosphate dehydrogen-ase. Metab. Eng. 25(0): 30-37. doi: 10.1016/j.ymben.2014.06.005
27. Nagaraja P, Yathirajan H S, Vasantha R A (2003) Highly sensitive reaction of tryptophan with p-phenylenediamine. Anal. Biochem. 312(2): 157-161. doi: 10.1016/S0003-2697(02)00504-3
28. Hennig M, Darimont B, Jansonius J et al. (2002) The Catalytic Mechanism of Indole-3-glycerol Phosphate Synthase: Crystal Structures of Complexes of the Enzyme from *Sulfolobus solfataricus* with Substrate Analogue, Substrate, and Product. J. Mol. Biol. 319(3): 757-766. doi: 10.1016/S0022-2836(02)00378-9
29. Wilmanns M, Priestle J P, Niermann T et al. (1992) Three-dimensional structure of the bifunctional enzyme phosphoribosylanthranilate isomerase: indoleglycerolphosphate synthase from *Escherichia coli* refined at 2.0 A resolution. Journal of Molecular Biology 223(2): 477-507
30. Eberhard M, Tsai-Pflugfelder M, Bolewska K et al. (1995) Indoleglycerol phosphate syn-thase-phosphoribosyl anthranilate isomerase: comparison of the bifunctional enzyme from *Escherichia coli* with engineered monofunctional domains. Biochemistry 34(16): 5419-5428
31. Darimont B, Stehlin C, Szadkoski H et al. (1998) Mutational analysis of the active site of indoleglycerol phosphate synthase from *Escherichia coli*. Protein Sci. 7(5): 1221-1232. doi: 10.1002/pro.5560070518

The invention claimed is:

1. An *Escherichia coli* cell being genetically modified to express an indole-3-glycerol phosphate synthase, IGPs, the IGPs being less sensitive to inhibition by anthranilate compared to the wild type IGPs of the *Escherichia coli* cell, wherein the IGPs has the sequence of one of SEQ ID NO: 2, SEQ ID NO: 4, SEQ ID NO: 5, or SEQ ID NO: 30.

2. An isolated or synthetic enzyme having the sequence of one of SEQ ID NO: 2, SEQ ID NO: 4, SEQ ID NO: 5, and SEQ ID NO: 30.

3. A method for the biotechnological production of L-tryptophan, comprising the steps of
   a) growing a genetically modified *Escherichia coli* cell, the cell being genetically modified to express an indole-3-glycerol phosphate synthase, IGPs, the IGPs being less sensitive to inhibition by anthranilate compared to the wild type IGPs of the bacterial cell, wherein the IGPs has
      alanine or glycine at position 60 instead of serine, or
      valine at position 8 instead of isoleucine, or
      phenylalanine at position 188 instead of leucine, or
      glutamine at position 58 instead of serine, valine at position 59 instead of proline, phenylalanine at position 60 instead of serine and glutamine at position 61 instead of lysine,
      compared to the sequence of SEQ ID NO: 1, in a suitable growth medium in a bioreactor, and separating L-tryptophan from the growth medium, or
   b) growing an *Escherichia coli* cell being genetically modified to express a heterologous enzyme having IGPs activity, the enzyme being less sensitive to inhibition by anthranilate compared to the wild type IGPs of the *Escherichia coli* cell, in a suitable growth medium in a bioreactor, and separating L-tryptophan from the growth medium, or
   c) using an enzyme having the sequence of one of SEQ ID NO: 2, SEQ ID NO: 3, SEQ ID NO: 4, SEQ ID NO: 5, or SEQ ID NO: 30, in biosynthesis of L-tryptophan in a suitable medium, and separating L-tryptophan from the medium.

4. The method according to claim 3, comprising the production of L-tryptophan in an industrial scale in a bioreactor.

5. The method according to claim 3, wherein the heterologous enzyme having IGPs activity is an enzyme from a *Saccharomyces* or *Aspergillus* species having an anthranilate synthase II domain.

6. The method according to claim 5, wherein the heterologous enzyme having IGPs activity is an enzyme from *Saccharomyces cerevisiae* or *Aspergillus niger* having an anthranilate synthase II domain.

* * * * *